United States Patent
Zhang et al.

(10) Patent No.: US 11,884,711 B2
(45) Date of Patent: Jan. 30, 2024

(54) FUSION PROTEINS OF GDF15 AND USE THEREOF

(71) Applicant: BEIJING QL BIOPHARMACEUTICAL CO., LTD., Beijing (CN)

(72) Inventors: Yuanyuan Zhang, Beijing (CN); Wei Guo, Beijing (CN); Xinyu Zhao, Beijing (CN); Haixia Zou, Beijing (CN); Yaoguang Jin, Beijing (CN); Xu Chen, Beijing (CN); Peng Zhai, Beijing (CN)

(73) Assignee: BEIJING QL BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/935,134

(22) Filed: Sep. 26, 2022

(65) Prior Publication Data
US 2023/0130599 A1  Apr. 27, 2023

Related U.S. Application Data

(63) Continuation of application No. PCT/CN2021/126453, filed on Oct. 26, 2021.

(30) Foreign Application Priority Data

Oct. 27, 2020 (WO) ............... PCT/CN2020/124031

(51) Int. Cl.
| | |
|---|---|
| C07K 14/495 | (2006.01) |
| A61P 3/04 | (2006.01) |
| C07K 16/18 | (2006.01) |
| A61K 38/00 | (2006.01) |
| A61K 39/00 | (2006.01) |

(52) U.S. Cl.
CPC ............. *C07K 14/495* (2013.01); *A61P 3/04* (2018.01); *C07K 16/18* (2013.01); *A61K 38/00* (2013.01); *A61K 2039/505* (2013.01); *C07K 2317/24* (2013.01); *C07K 2317/569* (2013.01); *C07K 2317/92* (2013.01); *C07K 2319/31* (2013.01)

(58) Field of Classification Search
None
See application file for complete search history.

(56) References Cited

U.S. PATENT DOCUMENTS

| | | |
|---|---|---|
| 9,272,019 B2 | 3/2016 | Shaw et al. |
| 10,195,250 B2 | 2/2019 | Lindhout et al. |
| 10,323,075 B2 | 6/2019 | Matern et al. |
| 10,336,798 B2 | 7/2019 | Xiong et al. |
| 10,752,664 B2 | 8/2020 | Xiong et al. |
| 10,894,814 B2 | 1/2021 | Xiong et al. |
| 11,105,818 B2 | 8/2021 | Su et al. |
| 2019/0000923 A1 | 1/2019 | Chutkow et al. |

FOREIGN PATENT DOCUMENTS

| | | | |
|---|---|---|---|
| CN | 103254309 A | 8/2013 | |
| CN | 104204218 A | 12/2014 | |
| CN | 106046168 A | 10/2016 | |
| CN | 106459222 A | 2/2017 | |
| CN | 108367053 A | 8/2018 | |
| CN | 109414471 A | 3/2019 | |
| CN | 109451726 A | 3/2019 | |
| CN | 110461870 A | 11/2019 | |
| CN | 111163795 A | 5/2020 | |
| WO | WO-2008028977 A2 * | 3/2008 | ............ A61P 25/00 |
| WO | 2015198199 A1 | 12/2015 | |
| WO | WO-2017196647 A1 * | 11/2017 | ............ A61K 38/16 |
| WO | WO-2021136223 A1 * | 7/2021 | ............ A61K 47/64 |
| WO | WO-2022089435 A1 * | 5/2022 | ............ A61P 3/04 |

OTHER PUBLICATIONS

Kotia et al., Anal Biochem., Apr. 15, 2010;399(2):190-5. doi: 10.1016/.ab.2010.01.008. Epub Jan. 13, 2010.*
Seung Joon Baek, et al. "Growth differentiation factor 15 (GDF15): A survival protein with therapeutic potential in metabolic diseases", Pharmacol Ther., vol. 198, Feb. 18, 2019(Feb. 18, 2019), ISSN:0163-7258 *the whole document*.
Anthony P Coll, et al. "GDF15 mediates the effects of metformin on body weight and energy balance", Nature, Dec. 2019(Dec. 25, 2019), No. 7795, vol. 578, ISSN: 1476-4687 *the whole document*.
International Search Report of the PCT application PCT/CN2021/126453, dated Jan. 28, 2022.
First Office Action of the corresponding Chinese application 202180019159.6, dated Dec. 16, 2022.

* cited by examiner

*Primary Examiner* — Michael Szperka
(74) *Attorney, Agent, or Firm* — Jun He Law Offices P.C.; James J. Zhu

(57) ABSTRACT

The present disclosure provides fusion polypeptides comprising serum albumin binding single domain antibody and GDF15, the polypeptide complexes thereof. Pharmaceutical compositions comprising the same and methods of treating diseases are also provided.

23 Claims, 8 Drawing Sheets

Specification includes a Sequence Listing.

Linkers

| SEQ ID NO | Liner Sequence |
|---|---|
| 17 | GQEP |
| 46 | GQEPGQEP |
| 47 | GQEPGQEPGQEPGQEPGQEP |
| 48 | GAQPGAQPGAQPGAQPGAQPGAQPGAQPGAQPGQEPGAQP GQEPGAQPGQEPGAQPGQEPGAQPGQEPGAQPGQEPGAQP |
| 49 | GAQPGAQPGAQPGQEPGQEPGQEPGQEPGQEPGQEPGQEP |
| 61 | GAQPGAQPGQEPGQEPGQEPGQEPGQEPGQEPGQEPGAQP |

Linkers Repeats

| SEQ ID NO | Linker repeats |
|---|---|
| 15 | GQEPGAQP |
| 16 | GAQPGAQP |
| 17 | GQEP |
| 18 | GAQP |
| 19 | GAQPGQEPGAQP |
| 20 | GAQPGQEP |
| 21 | GEQP |
| 22 | GPQE |
| 23 | GPEQ |
| 24 | GSEP |
| 25 | GESP |
| 26 | GPSE |
| 27 | GPES |
| 28 | GQAP |
| 29 | GPAQ |
| 30 | GPQA |
| 31 | GSQP |
| 32 | GASP |
| 33 | GPAS |
| 34 | GPSA |
| 35 | GGGS |
| 36 | GSGS |
| 37 | GGGGS |
| 38 | GQEPGQAP |
| 39 | GQAPGQEP |
| 40 | SEPATSGSETPGTSESATPESGPGTSTEPSEG |
| 41 | SEPATS |
| 42 | GSETPG |
| 43 | TSESAT |
| 44 | PESGPG |
| 45 | TSTEPS |

Figure 4a

Serum Albumin Binding Single Domain Antibody

| SEQ ID NO | Sequence of Serum Albumin Binding Single Domain Antibody |
|---|---|
| 4 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 5 | AEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 6 | SEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 7 | AGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 8 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |

GDF15

| SEQ ID NO | GDF15 amino acid sequence |
|---|---|
| 9 | ARNGDHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI |
| 10 | ARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 11 | GDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 12 | ARQGDHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI |
| 14 | ARNGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Figure 4b

Fusion polypeptide

| SEQ ID NO | Fusion polypeptide sequence |
|---|---|
| 50 | AEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 51 | AEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPGAQPGAQPGAQPGQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 52 | SEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 53 | AGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 54 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 55 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPGAQPGAQPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 56 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Figure 4c

| 57 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
|---|---|
| 58 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 59 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGQEPGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 13 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPGAQPGAQPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 60 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGQEPGQEPGQEPGQEPGQEPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Figure 4d

SEQUENCE LISTING

```
Sequence total quantity: 61
SEQ ID NO: 1              moltype = AA  length = 5
FEATURE                   Location/Qualifiers
REGION                    1..5
                          note = US8188223B2 SEQ ID NO:10 (CDR1)
source                    1..5
                          mol_type = protein
                          organism = synthetic construct
SEQUENCE: 1
SFGMS                                                                     5

SEQ ID NO: 2              moltype = AA  length = 17
FEATURE                   Location/Qualifiers
REGION                    1..17
                          note = US8188223B2 SEQ ID NO:24 (CDR2)
source                    1..17
                          mol_type = protein
                          organism = synthetic construct
SEQUENCE: 2
SISGSGSDTL YADSVKG                                                       17

SEQ ID NO: 3              moltype = AA  length = 6
FEATURE                   Location/Qualifiers
REGION                    1..6
                          note = US8188223B2 SEQ ID NO:38 (CDR3)
source                    1..6
                          mol_type = protein
                          organism = synthetic construct
SEQUENCE: 3
GGSLSR                                                                    6

SEQ ID NO: 4              moltype = AA  length = 115
FEATURE                   Location/Qualifiers
REGION                    1..115
                          note = US8188223B2 SEQ ID NO:62 (ALB8)
source                    1..115
                          mol_type = protein
                          organism = synthetic construct
SEQUENCE: 4
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSS       115

SEQ ID NO: 5              moltype = AA  length = 116
FEATURE                   Location/Qualifiers
REGION                    1..116
                          note = A-ALB8
```

```
source                  1..116
                        mol_type = protein
                        organism = synthetic construct
SEQUENCE: 5
AEVQLVESGG GLVQPGNSLR LSCAASGFTF SSFGMSWVRQ APGKGLEWVS SISGSGSDTL    60
YADSVKGRFT ISRDNAKTTL YLQMNSLRPE DTAVYYCTIG GSLSRSSQGT LVTVSS       116

SEQ ID NO: 6            moltype = AA   length = 116
FEATURE                 Location/Qualifiers
REGION                  1..116
                        note = S-ALB8
source                  1..116
                        mol_type = protein
                        organism = synthetic construct
SEQUENCE: 6
SEVQLVESGG GLVQPGNSLR LSCAASGFTF SSFGMSWVRQ APGKGLEWVS SISGSGSDTL    60
YADSVKGRFT ISRDNAKTTL YLQMNSLRPE DTAVYYCTIG GSLSRSSQGT LVTVSS       116

SEQ ID NO: 7            moltype = AA   length = 117
FEATURE                 Location/Qualifiers
REGION                  1..117
                        note = AG-ALB8
source                  1..117
                        mol_type = protein
                        organism = synthetic construct
SEQUENCE: 7
AGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSS      117

SEQ ID NO: 8            moltype = AA   length = 117
FEATURE                 Location/Qualifiers
REGION                  1..117
                        note = SG-ALB8
source                  1..117
                        mol_type = protein
                        organism = synthetic construct
SEQUENCE: 8
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSS      117

SEQ ID NO: 9            moltype = AA   length = 112
FEATURE                 Location/Qualifiers
REGION                  1..112
                        note = WT
source                  1..112
                        mol_type = protein
                        organism = synthetic construct
SEQUENCE: 9
ARNGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 10           moltype = AA   length = 112
FEATURE                 Location/Qualifiers
REGION                  1..112
                        note = N3QM57L
source                  1..112
                        mol_type = protein
                        organism = synthetic construct
SEQUENCE: 10
ARQGDHCPLG PGRCCRLHTV RASLEDLGWA DWVLSPREVQ VTMCIGACPS QFRAANLHAQ    60
IKTSLHRLKP DTVPAPCCVP ASYNPMVLIQ KTDTGVSLQT YDDLLAKDCH CI           112

SEQ ID NO: 11           moltype = AA   length = 109
FEATURE                 Location/Qualifiers
REGION                  1..109
                        note = del 1-3, M57L
source                  1..109
                        mol_type = protein
                        organism = synthetic construct
SEQUENCE: 11
GDHCPLGPGR CCRLHTVRAS LEDLGWADWV LSPREVQVTM CIGACPSQFR AANLHAQIKT    60
SLHRLKPDTV PAPCCVPASY NPMVLIQKTD TGVSLQTYDD LLAKDCHCI               109

SEQ ID NO: 12           moltype = AA   length = 112
FEATURE                 Location/Qualifiers
REGION                  1..112
                        note = N3Q
source                  1..112
                        mol_type = protein
```

```
                                organism    = synthetic construct
SEQUENCE: 12
ARQGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 13                   moltype = AA  length = 307
FEATURE                         Location/Qualifiers
REGION                          1..307
                                note = ALB8-linker80(47)-GDF15 (N3Q, M57L)
source                          1..307
                                mol_type    = protein
                                organism    = synthetic construct
SEQUENCE: 13
EVQLVESGGG LVQPGNSLRL SCAASGFTFS SFGMSWVRQA PGKGLEWVSS ISGSGSDTLY    60
ADSVKGRFTI SRDNAKTTLY LQMNSLRPED TAVYYCTIGG SLSRSSQGTL VTVSSGAQPG   120
AQPGAQPGAQ PGAQPGAQPG AQPGAQPGQE PGAQPGQEPG AQPGQEPGAQ PGQEPGAQPG   180
QEPGAQPGQE PGAQPARQGD HCPLGPGRCC RLHTVRASLE DLGWADWVLS PREVQVTMCI   240
GACPSQFRAA NLHAQIKTSL HRLKPDTVPA PCCVPASYNP MVLIQKTDTG VSLQTYDDLL   300
AKDCHCI                                                             307

SEQ ID NO: 14                   moltype = AA  length = 112
FEATURE                         Location/Qualifiers
REGION                          1..112
                                note = M57L
source                          1..112
                                mol_type    = protein
                                organism    = synthetic construct
SEQUENCE: 14
ARNGDHCPLG PGRCCRLHTV RASLEDLGWA DWVLSPREVQ VTMCIGACPS QFRAANLHAQ    60
IKTSLHRLKP DTVPAPCCVP ASYNPMVLIQ KTDTGVSLQT YDDLLAKDCH CI           112

SEQ ID NO: 15                   moltype = AA  length = 8
FEATURE                         Location/Qualifiers
REGION                          1..8
                                note = Synthetic
source                          1..8
                                mol_type    = protein
                                organism    = synthetic construct
SEQUENCE: 15
GQEPGAQP                                                              8

SEQ ID NO: 16                   moltype = AA  length = 8
FEATURE                         Location/Qualifiers
REGION                          1..8
                                note = Synthetic
source                          1..8
                                mol_type    = protein
                                organism    = synthetic construct
SEQUENCE: 16
GAQPGAQP                                                              8

SEQ ID NO: 17                   moltype = AA  length = 4
FEATURE                         Location/Qualifiers
REGION                          1..4
                                note = Synthetic
source                          1..4
                                mol_type    = protein
                                organism    = synthetic construct
SEQUENCE: 17
GQEP                                                                  4

SEQ ID NO: 18                   moltype = AA  length = 4
FEATURE                         Location/Qualifiers
REGION                          1..4
                                note = Synthetic
source                          1..4
                                mol_type    = protein
                                organism    = synthetic construct
SEQUENCE: 18
GAQP                                                                  4

SEQ ID NO: 19                   moltype = AA  length = 12
FEATURE                         Location/Qualifiers
REGION                          1..12
                                note = Synthetic
source                          1..12
                                mol_type    = protein
                                organism    = synthetic construct
SEQUENCE: 19
```

```
GAQPGQEPGA QP                                                                     12

SEQ ID NO: 20         moltype = AA  length = 8
FEATURE               Location/Qualifiers
REGION                1..8
                      note = Synthetic
source                1..8
                      mol_type = protein
                      organism = synthetic construct
SEQUENCE: 20
GAQPGQEP                                                                           8

SEQ ID NO: 21         moltype = AA  length = 4
FEATURE               Location/Qualifiers
REGION                1..4
                      note = Synthetic
source                1..4
                      mol_type = protein
                      organism = synthetic construct
SEQUENCE: 21
GEQP                                                                               4

SEQ ID NO: 22         moltype = AA  length = 4
FEATURE               Location/Qualifiers
REGION                1..4
                      note = Synthetic
source                1..4
                      mol_type = protein
                      organism = synthetic construct
SEQUENCE: 22
GPQE                                                                               4

SEQ ID NO: 23         moltype = AA  length = 4
FEATURE               Location/Qualifiers
REGION                1..4
                      note = Synthetic
source                1..4
                      mol_type = protein
                      organism = synthetic construct
SEQUENCE: 23
GPEQ                                                                               4

SEQ ID NO: 24         moltype = AA  length = 4
FEATURE               Location/Qualifiers
REGION                1..4
                      note = Synthetic
source                1..4
                      mol_type = protein
                      organism = synthetic construct
SEQUENCE: 24
GSEP                                                                               4

SEQ ID NO: 25         moltype = AA  length = 4
FEATURE               Location/Qualifiers
REGION                1..4
                      note = Synthetic
source                1..4
                      mol_type = protein
                      organism = synthetic construct
SEQUENCE: 25
GESP                                                                               4

SEQ ID NO: 26         moltype = AA  length = 4
FEATURE               Location/Qualifiers
REGION                1..4
                      note = Synthetic
source                1..4
                      mol_type = protein
                      organism = synthetic construct
SEQUENCE: 26
GPSE                                                                               4

SEQ ID NO: 27         moltype = AA  length = 4
FEATURE               Location/Qualifiers
REGION                1..4
                      note = Synthetic
source                1..4
                      mol_type = protein
                      organism = synthetic construct
```

```
SEQUENCE: 27
GPES                                                                                    4

SEQ ID NO: 28           moltype = AA  length = 4
FEATURE                 Location/Qualifiers
REGION                  1..4
                        note = Synthetic
source                  1..4
                        mol_type = protein
                        organism = synthetic construct
SEQUENCE: 28
GQAP                                                                                    4

SEQ ID NO: 29           moltype = AA  length = 4
FEATURE                 Location/Qualifiers
REGION                  1..4
                        note = Synthetic
source                  1..4
                        mol_type = protein
                        organism = synthetic construct
SEQUENCE: 29
GPAQ                                                                                    4

SEQ ID NO: 30           moltype = AA  length = 4
FEATURE                 Location/Qualifiers
REGION                  1..4
                        note = Synthetic
source                  1..4
                        mol_type = protein
                        organism = synthetic construct
SEQUENCE: 30
GPQA                                                                                    4

SEQ ID NO: 31           moltype = AA  length = 4
FEATURE                 Location/Qualifiers
REGION                  1..4
                        note = Synthetic
source                  1..4
                        mol_type = protein
                        organism = synthetic construct
SEQUENCE: 31
GSQP                                                                                    4

SEQ ID NO: 32           moltype = AA  length = 4
FEATURE                 Location/Qualifiers
REGION                  1..4
                        note = Synthetic
source                  1..4
                        mol_type = protein
                        organism = synthetic construct
SEQUENCE: 32
GASP                                                                                    4

SEQ ID NO: 33           moltype = AA  length = 4
FEATURE                 Location/Qualifiers
REGION                  1..4
                        note = Synthetic
source                  1..4
                        mol_type = protein
                        organism = synthetic construct
SEQUENCE: 33
GPAS                                                                                    4

SEQ ID NO: 34           moltype = AA  length = 4
FEATURE                 Location/Qualifiers
REGION                  1..4
                        note = Synthetic
source                  1..4
                        mol_type = protein
                        organism = synthetic construct
SEQUENCE: 34
GPSA                                                                                    4

SEQ ID NO: 35           moltype = AA  length = 4
FEATURE                 Location/Qualifiers
REGION                  1..4
                        note = Synthetic
source                  1..4
                        mol_type = protein
```

```
                        organism = synthetic construct
SEQUENCE: 35
GGGS                                                                          4

SEQ ID NO: 36           moltype = AA  length = 4
FEATURE                 Location/Qualifiers
REGION                  1..4
                        note = Synthetic
source                  1..4
                        mol_type = protein
                        organism = synthetic construct
SEQUENCE: 36
GSGS                                                                          4

SEQ ID NO: 37           moltype = AA  length = 5
FEATURE                 Location/Qualifiers
REGION                  1..5
                        note = Synthetic
source                  1..5
                        mol_type = protein
                        organism = synthetic construct
SEQUENCE: 37
GGGGS                                                                         5

SEQ ID NO: 38           moltype = AA  length = 8
FEATURE                 Location/Qualifiers
REGION                  1..8
                        note = Synthetic
source                  1..8
                        mol_type = protein
                        organism = synthetic construct
SEQUENCE: 38
GQEPGQAP                                                                      8

SEQ ID NO: 39           moltype = AA  length = 8
FEATURE                 Location/Qualifiers
REGION                  1..8
                        note = Synthetic
source                  1..8
                        mol_type = protein
                        organism = synthetic construct
SEQUENCE: 39
GQAPGQEP                                                                      8

SEQ ID NO: 40           moltype = AA  length = 32
FEATURE                 Location/Qualifiers
REGION                  1..32
                        note = Synthetic
source                  1..32
                        mol_type = protein
                        organism = synthetic construct
SEQUENCE: 40
SEPATSGSET PGTSESATPE SGPGTSTEPS EG                                           32

SEQ ID NO: 41           moltype = AA  length = 6
FEATURE                 Location/Qualifiers
REGION                  1..6
                        note = Synthetic
source                  1..6
                        mol_type = protein
                        organism = synthetic construct
SEQUENCE: 41
SEPATS                                                                        6

SEQ ID NO: 42           moltype = AA  length = 6
FEATURE                 Location/Qualifiers
REGION                  1..6
                        note = Synthetic
source                  1..6
                        mol_type = protein
                        organism = synthetic construct
SEQUENCE: 42
GSETPG                                                                        6

SEQ ID NO: 43           moltype = AA  length = 6
FEATURE                 Location/Qualifiers
REGION                  1..6
                        note = Synthetic
source                  1..6
```

```
                        mol_type = protein
                        organism = synthetic construct
SEQUENCE: 43
TSESAT                                                                    6

SEQ ID NO: 44           moltype = AA  length = 6
FEATURE                 Location/Qualifiers
REGION                  1..6
                        note = Synthetic
source                  1..6
                        mol_type = protein
                        organism = synthetic construct
SEQUENCE: 44
PESGPG                                                                    6

SEQ ID NO: 45           moltype = AA  length = 6
FEATURE                 Location/Qualifiers
REGION                  1..6
                        note = Synthetic
source                  1..6
                        mol_type = protein
                        organism = synthetic construct
SEQUENCE: 45
TSTEPS                                                                    6

SEQ ID NO: 46           moltype = AA  length = 8
FEATURE                 Location/Qualifiers
REGION                  1..8
                        note = Synthetic: (GQEP)2
source                  1..8
                        mol_type = protein
                        organism = synthetic construct
SEQUENCE: 46
GQEPGQEP                                                                  8

SEQ ID NO: 47           moltype = AA  length = 20
FEATURE                 Location/Qualifiers
REGION                  1..20
                        note = Synthetic:(GQEP)5
source                  1..20
                        mol_type = protein
                        organism = synthetic construct
SEQUENCE: 47
GQEPGQEPGQ EPGQEPGQEP                                                    20

SEQ ID NO: 48           moltype = AA  length = 80
FEATURE                 Location/Qualifiers
REGION                  1..80
                        note = Synthetic:(GAQP)8(GQEPGAQP)6
source                  1..80
                        mol_type = protein
                        organism = synthetic construct
SEQUENCE: 48
GAQPGAQPGA QPGAQPGAQP GAQPGAQPGA QPGQEPGAQP GQEPGAQPGQ EPGAQPGQEP         60
GAQPGQEPGA QPGQEPGAQP                                                    80

SEQ ID NO: 49           moltype = AA  length = 40
FEATURE                 Location/Qualifiers
REGION                  1..40
                        note = Synthetic:(GAQP)3(GQEP)7
source                  1..40
                        mol_type = protein
                        organism = synthetic construct
SEQUENCE: 49
GAQPGAQPGA QPGQEPGQEP GQEPGQEPGQ EPGQEPGQEP                              40

SEQ ID NO: 50           moltype = AA  length = 268
FEATURE                 Location/Qualifiers
REGION                  1..268
                        note = A-ALB8-linker40(17)-GDF15 (N3Q, M57L)
source                  1..268
                        mol_type = protein
                        organism = synthetic construct
SEQUENCE: 50
AEVQLVESGG GLVQPGNSLR LSCAASGFTF SSFGMSWVRQ APGKGLEWVS SISGSGSDTL         60
YADSVKGRFT ISRDNAKTTL YLQMNSLRPE DTAVYYCTIG GSLSRSSQGT LVTVSSGAQP        120
GAQPGAQPGQ EPGQEPGQEP GQEPGQEPGQ EPGQEPARQG DHCPLGPGRC CRLHTVRASL        180
EDLGWADWVL SPREVQVTMC IGACPSQFRA ANLHAQIKTS LHRLKPDTVP APCCVPASYN        240
PMVLIQKTDT GVSLQTYDDL LAKDCHCI                                          268
```

| SEQ ID NO: 51 | moltype = AA length = 308 |
| --- | --- |
| FEATURE | Location/Qualifiers |
| REGION | 1..308 |
| | note = A-ALB8-linker80(47)-GDF15 (N3Q, M57L) |
| source | 1..308 |
| | mol_type = protein |
| | organism = synthetic construct |

SEQUENCE: 51
```
AEVQLVESGG GLVQPGNSLR LSCAASGFTF SSFGMSWVRQ APGKGLEWVS SISGSGSDTL   60
YADSVKGRFT ISRDNAKTTL YLQMNSLRPE DTAVYYCTIG GSLSRSSQGT LVTVSSGAQP  120
GAQPGAQPGA QPGAQPGAQP GAQPGAQPGQ EPGAQPGQEP GAQPGQEPGA QPGQEPGAQP  180
GQEPGAQPGQ EPGAQPARQG DHCPLGPGRC CRLHTVRASL EDLGWADWVL SPREVQVTMC  240
IGACPSQFRA ANLHAQIKTS LHRLKPDTVP APCCVPASYN PMVLIQKTDT GVSLQTYDDL  300
LAKDCHCI                                                          308
```

| SEQ ID NO: 52 | moltype = AA length = 268 |
| --- | --- |
| FEATURE | Location/Qualifiers |
| REGION | 1..268 |
| | note = S-ALB8-linker40(17)-GDF15 (N3Q, M57L) |
| source | 1..268 |
| | mol_type = protein |
| | organism = synthetic construct |

SEQUENCE: 52
```
SEVQLVESGG GLVQPGNSLR LSCAASGFTF SSFGMSWVRQ APGKGLEWVS SISGSGSDTL   60
YADSVKGRFT ISRDNAKTTL YLQMNSLRPE DTAVYYCTIG GSLSRSSQGT LVTVSSGAQP  120
GAQPGAQPGQ EPGQEPGQEP GQEPGQEPGQ EPGQEPARQG DHCPLGPGRC CRLHTVRASL  180
EDLGWADWVL SPREVQVTMC IGACPSQFRA ANLHAQIKTS LHRLKPDTVP APCCVPASYN  240
PMVLIQKTDT GVSLQTYDDL LAKDCHCI                                    268
```

| SEQ ID NO: 53 | moltype = AA length = 269 |
| --- | --- |
| FEATURE | Location/Qualifiers |
| REGION | 1..269 |
| | note = AG-ALB8-linker40(17)-GDF15 (N3Q, M57L) |
| source | 1..269 |
| | mol_type = protein |
| | organism = synthetic construct |

SEQUENCE: 53
```
AGEVQLVESG GLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PGAQPGAQPG QEPGQEPGQE PGQEPGQEPG QEPGQEPARQ GDHCPLGPGR CCRLHTVRAS  180
LEDLGWADWV LSPREVQVTM CIGACPSQFR AANLHAQIKT SLHRLKPDTV PAPCCVPASY  240
NPMVLIQKTD TGVSLQTYDD LLAKDCHCI                                   269
```

| SEQ ID NO: 54 | moltype = AA length = 269 |
| --- | --- |
| FEATURE | Location/Qualifiers |
| REGION | 1..269 |
| | note = SG-ALB8-linker40(17)-GDF15 (N3Q, M57L) |
| source | 1..269 |
| | mol_type = protein |
| | organism = synthetic construct |

SEQUENCE: 54
```
SGEVQLVESG GLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PGAQPGAQPG QEPGQEPGQE PGQEPGQEPG QEPGQEPARQ GDHCPLGPGR CCRLHTVRAS  180
LEDLGWADWV LSPREVQVTM CIGACPSQFR AANLHAQIKT SLHRLKPDTV PAPCCVPASY  240
NPMVLIQKTD TGVSLQTYDD LLAKDCHCI                                   269
```

| SEQ ID NO: 55 | moltype = AA length = 309 |
| --- | --- |
| FEATURE | Location/Qualifiers |
| REGION | 1..309 |
| | note = SG-ALB8-linker80(47)-GDF15 (N3Q, M57L) |
| source | 1..309 |
| | mol_type = protein |
| | organism = synthetic construct |

SEQUENCE: 55
```
SGEVQLVESG GGLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PGAQPGAQPG AQPGAQPGAQ PGAQPGAQPG QEPGAQPGQE PGAQPGQEPG AQPGQEPGAQ  180
PGQEPGAQPG QEPGAQPARQ GDHCPLGPGR CCRLHTVRAS LEDLGWADWV LSPREVQVTM  240
CIGACPSQFR AANLHAQIKT SLHRLKPDTV PAPCCVPASY NPMVLIQKTD TGVSLQTYDD  300
LLAKDCHCI                                                          309
```

| SEQ ID NO: 56 | moltype = AA length = 249 |
| --- | --- |
| FEATURE | Location/Qualifiers |
| REGION | 1..249 |
| | note = SG-ALB8-linker20-GDF15 (N3Q, M57L) |
| source | 1..249 |
| | mol_type = protein |

```
                        organism = synthetic construct
SEQUENCE: 56
SGEVQLVESG GGLVQPGNSL RLSCAASGFT FSSFGMSWVR QAPGKGLEWV SSISGSGSDT     60
LYADSVKGRF TISRDNAKTT LYLQMNSLRP EDTAVYYCTI GGSLSRSSQG TLVTVSSGQE    120
PGQEPGQEPG QEPGQEPARQ GDHCPLGPGR CCRLHTVRAS LEDLGWADWV LSPREVQVTM    180
CIGACPSQFR AANLHAQIKT SLHRLKPDTV PAPCCVPASY NPMVLIQKTD TGVSLQTYDD    240
LLAKDCHCI                                                            249

SEQ ID NO: 57           moltype = AA  length = 237
FEATURE                 Location/Qualifiers
REGION                  1..237
                        note = SG-ALB8-linker8-GDF15 (N3Q, M57L)
source                  1..237
                        mol_type = protein
                        organism = synthetic construct
SEQUENCE: 57
SGEVQLVESG GGLVQPGNSL RLSCAASGFT FSSFGMSWVR QAPGKGLEWV SSISGSGSDT     60
LYADSVKGRF TISRDNAKTT LYLQMNSLRP EDTAVYYCTI GGSLSRSSQG TLVTVSSGQE    120
PGQEPARQGD HCPLGPGRCC RLHTVRASLE DLGWADWVLS PREVQVTMCI GACPSQFRAA    180
NLHAQIKTSL HRLKPDTVPA PCCVPASYNP MVLIQKTDTG VSLQTYDDLL AKDCHCI       237

SEQ ID NO: 58           moltype = AA  length = 233
FEATURE                 Location/Qualifiers
REGION                  1..233
                        note = SG-ALB8-linker4-GDF15 (N3Q, M57L)
source                  1..233
                        mol_type = protein
                        organism = synthetic construct
SEQUENCE: 58
SGEVQLVESG GGLVQPGNSL RLSCAASGFT FSSFGMSWVR QAPGKGLEWV SSISGSGSDT     60
LYADSVKGRF TISRDNAKTT LYLQMNSLRP EDTAVYYCTI GGSLSRSSQG TLVTVSSGQE    120
PARQGDHCPL GPGRCCRLHT VRASLEDLGW ADWVLSPREV QVTMCIGACP SQFRAANLHA    180
QIKTSLHRLK PDTVPAPCCV PASYNPMVLI QKTDTGVSLQ TYDDLLAKDC HCI            233

SEQ ID NO: 59           moltype = AA  length = 267
FEATURE                 Location/Qualifiers
REGION                  1..267
                        note = ALB8-linker40(17)-GDF15 (N3Q, M57L)
source                  1..267
                        mol_type = protein
                        organism = synthetic construct
SEQUENCE: 59
EVQLVESGGG LVQPGNSLRL SCAASGFTFS SFGMSWVRQA PGKGLEWVSS ISGSGSDTLY     60
ADSVKGRFTI SRDNAKTTLY LQMNSLRPED TAVYYCTIGG SLSRSSQGTL VTVSSGAQPG    120
AQPGAQPGQE PGQEPGQEPG QEPGQEPGQE PGQEPARQGD HCPLGPGRCC RLHTVRASLE    180
DLGWADWVLS PREVQVTMCI GACPSQFRAA NLHAQIKTSL HRLKPDTVPA PCCVPASYNP    240
MVLIQKTDTG VSLQTYDDLL AKDCHCI                                         267

SEQ ID NO: 60           moltype = AA  length = 269
FEATURE                 Location/Qualifiers
REGION                  1..269
                        note = SG-ALB8-linker40(25)-GDF15 (N3Q, M57L)
source                  1..269
                        mol_type = protein
                        organism = synthetic construct
SEQUENCE: 60
SGEVQLVESG GGLVQPGNSL RLSCAASGFT FSSFGMSWVR QAPGKGLEWV SSISGSGSDT     60
LYADSVKGRF TISRDNAKTT LYLQMNSLRP EDTAVYYCTI GGSLSRSSQG TLVTVSSGAQ    120
PGAQPGQEPG QEPGQEPGQE PGQEPGQEPG QEPGAQPARQ GDHCPLGPGR CCRLHTVRAS    180
LEDLGWADWV LSPREVQVTM CIGACPSQFR AANLHAQIKT SLHRLKPDTV PAPCCVPASY    240
NPMVLIQKTD TGVSLQTYDD LLAKDCHCI                                       269

SEQ ID NO: 61           moltype = AA  length = 40
FEATURE                 Location/Qualifiers
REGION                  1..40
                        note = Synthetic:(GAQP)2(GQEP)7(GAQP)
source                  1..40
                        mol_type = protein
                        organism = synthetic construct
SEQUENCE: 61
GAQPGAQPGQ EPGQEPGQEP GQEPGQEPGQ EPGQEPGAQP                            40
```

FUSION PROTEINS OF GDF15 AND USE THEREOF

SEQUENCE LISTING

The instant application contains a Sequence Listing which has been submitted electronically in XML format and is hereby incorporated by reference in its entirety. Said XML copy, created on Sep. 26, 2022, is named 074585-8006US01.xml and is 80,763 bytes in size.

FIELD OF THE INVENTION

The present invention relates to fusion proteins, pharmaceutical compositions thereof, and methods of using such to prevent and/or treat diseases.

BACKGROUND

Growth differentiation factor 15 (GDF15), also named as Macrophage inhibitory cytokine-1 or MIC-1, is a member of the transforming growth factor beta superfamily. The function of GDF15 is not fully understood. Existing studies show that GDF15 may have a role in regulating inflammatory pathways, participating in regulating apoptosis, cell repair and cell growth, which are biological processes observed in cardiovascular and neoplastic disorders. Other studies show that GDF15 possesses therapeutic utility in metabolic disorders such as obesity.

Metabolic disorders are commonly associated with insulin resistance, visceral adiposity, atherogenic dyslipidemia, etc., which pose major and escalating public health and clinical challenge worldwide. However, existing treatment for metabolic diseases faces problems such as short half-life and/or low efficacy.

Therefore, there is a need for an improved therapeutic solution for treating metabolic diseases.

SUMMARY OF THE INVENTION

Provided herein are fusion proteins of GDF15, and pharmaceutical compositions and methods of use for treating/preventing metabolic disorders.

In one aspect, the present disclosure provides a fusion polypeptide comprising:
a) a first polypeptide fragment comprising a serum albumin binding single domain antibody; and
b) a second polypeptide fragment comprising a GFRAL receptor agonist; wherein the first polypeptide fragment and the second polypeptide fragment are linked to one another directly or via a linker.

In some embodiments, the single domain antibody comprises a VHH domain.

In some embodiments, the VHH domain is humanized.

In some embodiments, the VHH domain comprises a complementarity determining region 1 (CDR1), CDR2 and CDR3, wherein the CDR1 comprises the sequence of SEQ ID NO: 1 or a variant thereof having up to 3, 2, or 1 amino acid mutation, a CDR2 comprising the sequence of SEQ ID NO: 2 or a variant thereof having up to 3, 2, or 1 amino acid mutation, and/or a CDR3 comprising the sequence of SEQ ID NO: 3 or a variant thereof having up to 3, 2, or 1 amino acid mutation, wherein the VHH domain retains the binding specificity to serum albumin, optionally to human serum albumin.

In some embodiments, the VHH domain comprises a complementarity determining region 1 (CDR1) comprising the sequence of SEQ ID NO: 1, a CDR2 comprising the sequence of SEQ ID NO: 2, and a CDR3 comprising the sequence of SEQ ID NO: 3.

In some embodiments, the VHH domain comprises the sequence of SEQ ID NO: 4, or a variant thereof having at least 70% (e.g. at least 75%, 80%, 85%, 90%, 95%, 99%) identity to SEQ ID NO: 4, wherein the variant retains the binding specificity and/or affinity to serum albumin.

In some embodiments, the variant of SEQ ID NO: 4 has up to 10, 9, 8, 7, 6, 5, 4, 3, 2, or 1 amino acid mutation relative to SEQ ID NO: 4.

In some embodiments, the serum albumin binding single domain antibody further comprises an N-terminal extension attached to the VHH domain.

In some embodiments, the N-terminal extension comprises amino acid residues of SG, AG, S or A.

In some embodiments, the serum albumin binding single domain antibody comprises a sequence selected from SEQ ID NOs: 4-8.

In some embodiments, the GFRAL receptor agonist comprises GDF15.

In some embodiments, the GDF15 comprises an amino acid sequence having at least 90% sequence identity to SEQ ID NO: 9 while retaining substantial biological activity of SEQ ID NO: 9.

In some embodiments, the GDF15 comprises no more than 10, 9, 8, 7, 6, 5, 4, 3, 2 mutations relative to SEQ ID NO: 9 while retaining substantial biological activity of SEQ ID NO: 9.

In some embodiments, the GDF15 comprises one or more mutations at a position selected from the group consisting of: A1, R2, N3, H6, P11, H18, T19, V20, R21, A30, M43, A47, R53, A54, M57, H66, R67, L68, A75, A81, P85, M86, Q90, T92, and L105, or any combination thereof, relative to SEQ ID NO: 9.

In some embodiments, the one or more mutations in GDF15 comprises:
1) mutation of N3 selected from the group consisting of: N3Q, N3S, N3E, N3A, N3T, N3P, N3G, N3V, N3H, N3Y and deletion of N3; and/or
2) substitution of M57 selected from the group consisting of: M57A, M57E and M57L; and/or
3) substitution of M86L or M86A.

In some embodiments, the one or more mutations in GDF15 are selected from the group consisting of: R2S, R2A, R2E, N3S, N3E, N3A, N3T, N3P, N3G, N3V, N3H, N3Y, N3Q, H6D, P11E, H18E, H18Q, T19S, V20L, R21E, A30E, M43L, M43E, A47E, R53E, A54E, M57A, M57E, M57L, H66E, R67E, L68E, A75E, A81E, P85E, M86F, M86A, M86L, Q90E, T92E, L105E, deletion of N3, and deletion of N-terminal 1-3 residues, or any combination thereof, relative to SEQ ID NO: 9.

In some embodiments, the GDF15 comprises or consists of an amino acid sequence selected from the group consisting of SEQ ID NOs: 9-12 and 14.

In some embodiments, the fusion polypeptide comprises from N terminus to C terminus, the serum albumin binding single domain antibody, the linker and the GDF15.

In some embodiments, the linker comprises a polypeptide linker.

In some embodiments, the polypeptide linker has a length of at least 4 amino acid residues (e.g. at least 4, 12, 24, 40, 50, 60, 70, 80, 90, 100, 110, or 120 amino acid resides).

In some embodiments, the polypeptide linker has a length of 4-80 or 20-80 or 30-80 or 40-80 amino acid residues.

In some embodiments, the polypeptide linker has a length of about 4, 8, 20, 40, 50, 60, 70 or 80 amino acid residues.

In some embodiments, the polypeptide linker comprises at least one acidic amino acid residue.

In some embodiments, the at least one acidic amino acid residue comprises glutamic acid (E).

In some embodiments, the polypeptide linker comprises one or more repeats of a repeating sequence.

In some embodiments, the repeating sequence consists of no more than 4, 5 or 6 types of amino acid residues selected from the group consisting of: G, Q, A, E, P, T and S.

In some embodiments, the repeating sequence comprises Q.

In some embodiments, the repeating sequence consists of G, Q, A, E, and P.

In some embodiments, the repeating sequence consists of a sequence selected from the group consisting of: SEQ ID NO: 15 (GQEPGAQP), SEQ ID NO: 16 (GAQPGAQP), SEQ ID NO: 17 (GQEP), SEQ ID NO: 18 (GAQP), SEQ ID NO: 40 (SEPATSGSETPGTSESATPESGPGTSTEPSEG), SEQ ID NO: 19 (GAQPGQEPGAQP), SEQ ID NO: 20 (GAQPGQEP), SEQ ID NO: 21 (GEQP), SEQ ID NO: 22 (GPQE), SEQ ID NO: 23 (GPEQ), SEQ ID NO: 24 (GSEP), SEQ ID NO: 25 (GESP), SEQ ID NO: 26 (GPSE), SEQ ID NO: 27 (GPES), SEQ ID NO: 28 (GQAP), SEQ ID NO: 29 (GPAQ), SEQ ID NO: 30 (GPQA), SEQ ID NO: 31 (GSQP), SEQ ID NO: 32 (GASP), SEQ ID NO: 33 (GPAS), SEQ ID NO: 34 (GPSA), SEQ ID NO: 35 (GGGS), SEQ ID NO: 36 (GSGS), SEQ ID NO: 37 (GGGGS), SEQ ID NO: 38 (GQEPGQAP), SEQ ID NO: 39: (GQAPGQEP), SEQ ID NO: 41 (SEPATS), SEQ ID NO: 42 (GSETPG), SEQ ID NO: 43 (TSESAT), SEQ ID NO: 44 (PESGPG), SEQ ID NO: 45 (TSTEPS) and GS.

In some embodiments, the polypeptide linker comprises (Repeat1)r(Repeat2)s(Repeat3)x(Repeat4)y, wherein Repeat1, Repeat2, Repeat3 and Repeat4 are linked via a peptide bond or via one or more amino acid residues, Repeat1, Repeat2, Repeat3 and Repeat4 independently, comprise or consist of a sequence selected from the group consisting of: SEQ ID NO: 15 (GQEPGAQP), SEQ ID NO: 16 (GAQPGAQP), SEQ ID NO: 17 (GQEP), SEQ ID NO: 18 (GAQP), SEQ ID NO: 40 (SEPATSGSETPGTSESATPESGPGTSTEPSEG), SEQ ID NO: 19 (GAQPGQEPGAQP), SEQ ID NO: 219 (GAQPGQEP), SEQ ID NO: 21 (GEQP), SEQ ID NO: 22 (GPQE), SEQ ID NO: 23 (GPEQ), SEQ ID NO: 24 (GSEP), SEQ ID NO: 25 (GESP), SEQ ID NO: 26 (GPSE), SEQ ID NO: 27 (GPES), SEQ ID NO: 28 (GQAP), SEQ ID NO: 29 (GPAQ), SEQ ID NO: 30 (GPQA), SEQ ID NO: 31 (GSQP), SEQ ID NO: 32 (GASP), SEQ ID NO: 33 (GPAS), SEQ ID NO: 34 (GPSA), SEQ ID NO: 35 (GGGS), SEQ ID NO: 36 (GSGS), SEQ ID NO: 37 (GGGGS), SEQ ID NO: 38 (GQEPGQAP), SEQ ID NO: 39 (GQAPGQEP), SEQ ID NO: 41 (SEPATS), SEQ ID NO: 42 (GSETPG), SEQ ID NO: 43 (TSESAT), SEQ ID NO: 44 (PESGPG), SEQ ID NO: 45 (TSTEPS) and GS, and r, s, x and y are independently an integer selected from 0 to 30, provided that r, s, x and y are not 0 at the same time.

In some embodiments, x and y are 0, r, and s are independently an integer selected from 1 to 30, and Repeat1 and Repeat2 are a combination selected from the group consisting of:
 a) Repeat1 comprises or consists of a sequence of SEQ ID NO: 15, Repeat2 comprises or consists of a sequence of SEQ ID NO: 18;
 b) Repeat1 comprises or consists of a sequence of SEQ ID NO: 17, Repeat2 comprises or consists of a sequence of SEQ ID NO: 18;
 c) Repeat1 comprises or consists of a sequence of SEQ ID NO: 18, Repeat2 comprises or consists of a sequence of SEQ ID NO: 17;
 d) Repeat1 comprises or consists of a sequence of SEQ ID NO: 18, Repeat2 comprises or consists of a sequence of SEQ ID NO: 15;
 e) Repeat1 comprises or consists of a sequence of SEQ ID NO: 19, Repeat2 comprises or consists of a sequence of SEQ ID NO: 18;
 f) Repeat1 comprises or consists of a sequence of SEQ ID NO: 40, Repeat2 comprises or consists of a sequence of SEQ ID NO: 18;
 g) Repeat1 comprises or consists of a sequence of SEQ ID NO: 18, Repeat2 comprises or consists of a sequence of SEQ ID NO: 38 and
 h) Repeat1 comprises or consists of a sequence of SEQ ID NO: 40, Repeat2 comprises or consists of a sequence of SEQ ID NO: 17.

In some embodiments, r, x and y are 0, s is an integer selected from 1 to 30, and Repeat1 comprises or consists of a sequence of SEQ ID NO: 17.

In some embodiments, y is 0, r, s and x are independently an integer selected from 1 to 30, and Repeat1, Repeat2, and Repeat 3 are a combination selected from the group consisting of:
 (a) Repeat1 comprises or consists of a sequence of SEQ ID NO: 18, Repeat2 comprises or consists of a sequence of SEQ ID NO: 19, and Repeat3 comprises or consists of a sequence of SEQ ID NO: 18;
 (b) Repeat1 comprises or consists of a sequence of SEQ ID NO: 18, Repeat2 comprises or consists of a sequence of SEQ ID NO: 17, and Repeat3 comprises or consists of a sequence of SEQ ID NO: 18;
 (c) Repeat1 comprises or consists of a sequence of SEQ ID NO: 40, Repeat2 comprises or consists of a sequence of SEQ ID NO: 17, and Repeat3 comprises or consists of a sequence of SEQ ID NO: 18;
 (d) Repeat1 comprises or consists of a sequence of SEQ ID NO: 40, Repeat2 comprises or consists of a sequence of SEQ ID NO: 18, and Repeat3 comprises or consists of a sequence of SEQ ID NO: 17;
 (e) Repeat1 comprises or consists of a sequence of SEQ ID NO: 15, Repeat2 comprises or consists of a sequence of SEQ ID NO: 28, and Repeat3 comprises or consists of a sequence of SEQ ID NO: 18;
 (f) Repeat1 comprises or consists of a sequence of SEQ ID NO: 18, Repeat2 comprises or consists of a sequence of SEQ ID NO: 38, and Repeat3 comprises or consists of a sequence of SEQ ID NO: 15;
 (g) Repeat1 comprises or consists of a sequence of SEQ ID NO: 18, Repeat2 comprises or consists of a sequence of SEQ ID NO: 15, and Repeat3 comprises or consists of a sequence of SEQ ID NO: 18;
 (h) Repeat1 comprises or consists of a sequence of SEQ ID NO: 17, Repeat2 comprises or consists of a sequence of SEQ ID NO: 15, and Repeat3 comprises or consists of a sequence of SEQ ID NO: 17; and
 (i) Repeat1 comprises or consists of a sequence of SEQ ID NO: 18, Repeat2 comprises or consists of a sequence of SEQ ID NO: 15, and Repeat3 comprises or consists of a sequence of SEQ ID NO: 38.

In some embodiments, r, s, x and y are independently an integer selected from 1 to 30, and Repeat1, Repeat2, Repeat 3 and Repeat 4 are a combination selected from the group consisting of:
 (a) Repeat1 comprises or consists of a sequence of SEQ ID NO: 18, Repeat2 comprises or consists of a sequence of SEQ ID NO: 20, Repeat3 comprises or consists of a sequence of SEQ ID NO: 17, and Repeat4 comprises or consists of a sequence of SEQ ID NO: 18;
(b) Repeat1 comprises or consists of a sequence of SEQ ID NO: 15, Repeat2 comprises or consists of a sequence of SEQ ID NO: 38, Repeat3 comprises or consists of a sequence of SEQ ID NO: 15, and Repeat4 comprises or consists of a sequence of SEQ ID NO: 18;
(c) Repeat1 comprises or consists of a sequence of SEQ ID NO: 18, Repeat2 comprises or consists of a sequence of SEQ ID NO: 38, Repeat3 comprises or consists of a sequence of SEQ ID NO: 15, and Repeat4 comprises or consists of a sequence of SEQ ID NO: 18;
(d) Repeat1 comprises or consists of a sequence of SEQ ID NO: 18, Repeat2 comprises or consists of a sequence of SEQ ID NO: 28, Repeat3 comprises or consists of a sequence of SEQ ID NO: 18, and Repeat4 comprises or consists of a sequence of SEQ ID NO: 15; and
(e) Repeat1 comprises or consists of a sequence of SEQ ID NO: 18, Repeat2 comprises or consists of a sequence of SEQ ID NO: 15, Repeat3 comprises or consists of a sequence of SEQ ID NO: 39, and Repeat4 comprises or consists of a sequence of SEQ ID NO: 38.

In some embodiments, the polypeptide linker comprises an amino acid sequence selected from the group consisting of SEQ ID NO: 17, 46-49 and 61.

In some embodiments, the fusion polypeptide comprises an amino acid sequence selected from the group consisting of: SEQ ID NOs: 50-60 and 13.

In another aspect, the present disclosure provides a polypeptide complex comprises a dimer of the fusion polypeptide provided herein.

In some embodiments, the polypeptide complex is a homo-dimer.

In some embodiments, the dimer is associated with a disulfide bond.

In some embodiments, the disulfide bond is formed between the second polypeptide fragments comprising the GDF15.

In another aspect, the present disclosure provides a polynucleotide encoding the fusion polypeptide provided herein, or the polypeptide complex provided herein.

In another aspect, the present disclosure provides a vector comprising the polynucleotide provided herein.

In another aspect, the present disclosure provides a host cell comprising the vector provided herein.

In some embodiments, the host cell is a prokaryotic cell or eukaryotic cell.

In another aspect, the present disclosure provides a method of producing the polypeptide complex provided herein, comprising culturing the host cell provided herein under a condition that allows expression of the polynucleotide provided herein.

In some embodiments, the host cell is prokaryotic cell or a eukaryotic cell.

In some embodiments, the polypeptide complex is expressed as inclusion bodies.

In some embodiments, the method further comprises renaturing the polypeptide complex from the inclusion bodies.

In another aspect, the present disclosure provides a pharmaceutical composition comprising the fusion polypeptide provided herein, or the polypeptide complex provided herein and a pharmaceutically acceptable carrier.

In another aspect, the present disclosure provides a method of preventing or treating a metabolic disorder in a subject in need thereof, comprising administering a therapeutically effective amount of the fusion polypeptide provided herein, or the polypeptide complex provided herein.

In some embodiments, the metabolic disorder is diabetes, obesity, non-alcoholic steatohepatitis (NASH), cardiovascular like dyslipidemia, artherosclerosis, alcoholic steatohepatitis (ASH), diabetic nephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Throughout the present disclosure, the articles "a," "an," and "the" are used herein to refer to one or to more than one (i.e., to at least one) of the grammatical object of the article. By way of example, "a fusion polypeptide" means one fusion polypeptide or more than one fusion polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

BRIEF DESCRIPTION OF THE FIGURES

FIG. 1a shows food intake upon the treatment of Fusion protein 1 or 2 from Day 1 to Day 11, with semaglutide as a control. FIG. 1b shows body weight loss upon the treatment of Fusion protein 1 or 2 from Day 1 to Day 11, with semaglutide as a control. FIG. 1c shows food intake upon the treatment of Fusion protein 5 or 12 from Day 1 to Day 11. FIG. 1d shows body weight loss upon the treatment of Fusion protein 5 or 12 from Day 1 to Day 11.

FIG. 3a shows food intake upon the treatment of Fusion protein 5 or 12 from Day 1 to Day 12. FIG. 3b shows body weight loss upon the treatment of Fusion protein 5 or 12 from Day 1 to Day 12.

FIGS. 4a to 4d show the sequences disclosed in the present disclosure.

FIGURE DETAILED DESCRIPTION

Figure 1A:
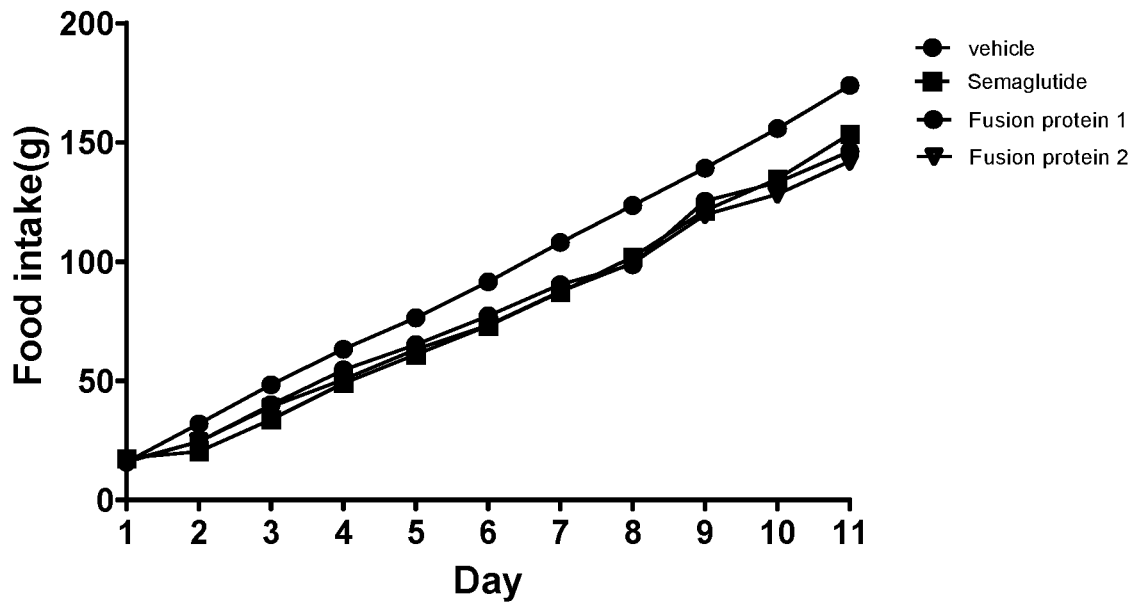
FIGS. 1a to 1d show in vivo activities of the tested fusion proteins in C57BL/6 mice.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

The term "amino acid" as used herein refers to an organic compound containing amine (—NH2) and carboxyl (—COOH) functional groups, along with a side chain specific to each amino acid. The names of amino acids are also represented as standard single letter or three-letter codes in the present disclosure.

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional form" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide. A variant may differ from the parent peptide by one or more amino acid residues. For example, a variant may have substitutions, additions, deletions, insertions, or truncations of one more amino acid residue of the parent polypeptide.

The term "fragment" as used herein refers to partial sequence of the parent polypeptide of any length. A fragment can still retain at least partial function of the parent polypeptide.

The term "derivative" as used herein refers to a chemically modified polypeptide or fusion polypeptide, in which one or more well-defined number of substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCl, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

Fusion Polypeptides

Provided herein are fusion proteins or fusion polypeptides comprising a serum albumin binding single domain antibody and a glial cell line-derived neurotrophic factor (GDNF) receptor alpha like (GFRAL receptor) agonist.

The term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence may be produced by genetic recombination of two encoding polynucleotide sequences, and can be expressed by a method of introducing a construct containing the recombinant polynucleotides into a host cell.

The term "protein" and "polypeptide" are used interchangeably herein and refer a polymer of amino acid residues linked by covalent bonds such as peptide bonds. A protein or polypeptide as provided herein can comprise naturally occurring or non-natural amino acid residues, or both. Polypeptides and proteins provided herein can comprise any suitable length of amino acid residues, for example, from at least 5, 10, 20, 30, 40, 50, 60, 70, 80, 90, 100, 200, 300, 400, 500, 600, 700, 800, 900, 1000, or more amino acid residues in length.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Trp or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, γ-carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., an αcarbon that is bound to a hydrogen, a carboxyl group, an amino group, and an R group, e.g., homoserine, norleucine, methionine sulfoxide, methionine methyl sulfonium. Such analogs can have modified R groups {e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofarnesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (Tle), b-alanine, 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Na-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl)carboxylic acid, and (1-aminocyclooctyl)carboxylic acid.

Introduction of non-natural amino acids into a fusion polypeptide, polypeptide fragment, and/or polypeptide complex may be realized by the technology described in Wang et al., Science 292:498-500, 2001; Deiters et al., J Am Chem Soc 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons, such as a four-base codon (e.g. AGGA, AGGU, CGGU, CGCU, CGAU, CCCU, CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice.

In certain embodiments, the fusion polypeptide is a single chain polypeptide. A single chain polypeptide can still have intrachain bonds within the molecule but does not include complexes formed by one or more interchain bonds.

In one aspect, the present disclosure provides a fusion polypeptide comprising: a) a first polypeptide fragment comprising a serum albumin binding single domain antibody; and b) a second polypeptide fragment comprising a glial cell line-derived neurotrophic factor (GDNF) receptor alpha like (GFRAL receptor) agonist; wherein the first polypeptide fragment and the second polypeptide fragment are linked to one another directly or via a linker.

The GFRAL receptor agonist in the fusion polypeptide functions as a therapeutic moiety and the serum albumin binding single domain antibody functions as a fusion partner to increase the half-life of the GFRAL receptor agonist. In some embodiments, the fusion polypeptide has a half-life that is at least 1.5 times (e.g., at least 2 times, at least 5 times, at least 10 times, at least 20 times, at least 30 times, at least 40 times, at least 50 times, at least 60 times, at least 70 times, at least 80 times, at least 90 times, at least 100 times, at least 150 times or at least 200 times) greater than the half-life of the corresponding therapeutic moiety per se in a given animal (e.g. a mouse, a monkey, a human, among others). In some embodiments, the fusion polypeptide has a half-life that is increased with more than 1 hour (e.g., more than 2 hours, more than 6 hours, more than 12 hours, more than 18 hours, more than 24 hours, more than one day, more than two days, more than 3 days, more than 4 days, more than 5 days, more than 6 days, more than 1 weeks, more than 2 weeks, more than three weeks, more than one month, more than two months, more than three months or more than 6 months) compared to the half-life of the corresponding therapeutic moiety per se in a given anima l (e.g. a mouse, a monkey, a human, among others). In some embodiments, the fusion protein has a half-life that is more than 5 hours (e.g., more than 6 hours, more than 12 hours, more than 18 hours, of about one day, two days, three days, four days, five days, six days, one week, two weeks, three weeks, one month, two months, three months or 6 months) in a given animal (e.g. a mouse, a monkey, a human, among others). In some embodiments, the fusion protein has a half-life that permits administration of the fusion protein at a frequency of no more than once per day, once every two days, once every three days, once per week, once every two weeks, once every three weeks, once every month, once every two months, once every three months, once every four months, or once six months in a given animal (e.g. a mouse, a monkey, a human, among others), yet still capable of proving therapeutic benefit.

The term "half-life" refers to the time taken for the serum concentration of a polypeptide (e.g., a fusion polypeptide) to be reduce by 50%. Methods for pharmacokinetic analysis and determination of half-life are familiar to those skilled in the art. Details may be found in Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd revised edition (1982).

Without being bound to any theory, the serum albumin binding single domain antibody may also provide for improved tissue targeting, tissue distribution, tissue penetration, diffusion within the tissue, and enhanced efficacy of the fusion polypeptide as compared with the therapeutic moiety per se.

Serum Albumin Binding Single Domain Antibody

The term "serum albumin" refers to an albumin (a type of globular protein) found in vertebrate blood. Serum albumin is produced by the liver, occurs dissolved in blood plasma and is the most abundant blood protein in mammals. Serum albumin typically has a half-life of around three weeks, which is mainly regulated by neonatal Fc receptor (FcRn). FcRn protects serum albumin from intracellular degradation by binding it with high affinity and diverting it from a lysosomal pathway, returning it to the extracellular compartment. In some embodiments, the serum albumin is selected from human serum albumin (HSA), cynomolgus monkeys serum albumin and mouse serum albumin. In some embodiments, the serum albumin provided herein is HSA.

The term "antibody" as used herein includes any immunoglobulin that binds to a specific antigen. conventional antibody (e.g., antibodies from human or mice) comprises two heavy (H) chains and two light (L) chains. The heavy chains are classified as $\alpha$, $\delta$, $\epsilon$, $\gamma$, and $\mu$, each heavy chain consists of a variable domain (VH domain) and a first, second, third, and optionally fourth constant region (CH1, CH2, CH3, CH4 respectively); The light chains are classified as $\lambda$ or $\kappa$, while each light chain consists of a variable domain (VL domain) and a constant domain. The antibody has a "Y" shape, with the stem of the Y consisting of the second and third constant domain of two heavy chains bound together via disulfide bonding. Each arm of the Y includes the variable domain and first constant domain of a single heavy chain bound to the variable and constant domains of a single light chain. The variable domains of the light and heavy chains are responsible for antigen binding. The variable domains in both chains generally contain three hypervariable regions called the complementarity determining regions (CDRs, namely CDR1, CDR2, and CDR3 of light chain or heavy chain). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.*, 273(4), 927 (1997); Chothia, C. et al., *J Mol Biol*. December 5; 186(3):651-63 (1985); Chothia, C. and Lesk, A. M., *J. Mol. Biol.*, 196,901 (1987); Chothia, C. et al., *Nature*. December 21-28; 342(6252):877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology*, 27: 55-77 (2003); Marie-Paule Lefranc et al., *Immunome Research*, 1(3), (2005); Marie-Paule Lefranc, Molecular Biology of B cells (second edition), chapter 26, 481-514, (2015)). The three CDRs are interposed between flanking stretches known as framework regions (FRs, namely FR1, FR2, FR3 and FR4 of light chain or heavy chain), which are more highly conserved than the CDRs and form a scaffold to support the highly variable loops. The constant domains of the heavy and light chains are not involved in antigen-binding, but exhibit various effector functions. Conventional antibodies are assigned to classes based on the amino acid sequences of the constant domains of their heavy chains.

The term "single domain antibody" refers to an antibody fragment containing a single variable domain of a heavy chain or a single variable domain of a light chain. A single domain antibody contains 3 complementarity determining regions (CDRs) and is capable of binding to a specific antigen (e.g., serum albumin).

The single variable domain can be derived from the variable domain of a camelid antibody (VHH domain), or the variable domain of cartilaginous fish antibody (VNAR domain). Both camelid antibodies and cartilaginous fish antibodies naturally lack light chains and consist of a pair of heavy chains. Alternatively, the single variable domain can be derived from the variable domain of a conventional antibody (e.g., from humans or mice) heavy chain (VH domain) or the variable domain of a common antibody light chain (VL domain). It is contemplated that a single domain antibody is fairly small in size, for example, has a molecular weight of no more than 25 kD, no more than 20 kD, no more than 15 kD, or no more than 10 kD.

The term "single domain antibody" is used herein in its broadest sense and is not limited to a specific biological source or to a specific method of preparation. For example, a single domain antibody can be obtained, for example (1) by isolating the VHH domain or VNAR domain of a naturally occurring heavy chain antibody; (2) by expression of a nucleotide sequence encoding a naturally occurring VHH domain or VNAR domain; (3) by "humanization" (as described below) of a naturally occurring VHH domain or VNAR domain or by expression of a nucleic acid encoding a such humanized VHH domain or VNAR domain; (4) by "camelization" of a naturally occurring VH domain from any animal species, in particular a species of mammal, such as from a human being, or by expression of a nucleic acid encoding such a camelized VH domain; 5) using synthetic or semi-synthetic techniques for preparing proteins, polypeptides or other amino acid sequences; and/or (6) by any combination of the foregoing. Suitable methods and techniques for performing the foregoing will be clear to the skilled person.

In some embodiments, the single domain antibody described herein comprises a VHH domain derived from antibodies raised in Camelidae species, for example in camel, dromedary, alpaca and guanaco. A single domain antibody comprising a VHH domain are highly soluble and highly stable to heat, pH, proteases and other denaturing agents or conditions.

In some embodiments, the first polypeptide fragment comprises one or more single domain antibody that is capable of specifically binding to serum albumin.

The term "binding specificity", "specific binding" or "specifically binds" in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. Antibodies or fragments thereof that immunospecifically bind to an antigen may be cross-reactive with related antigens, carrying the same epitope. The "binding specificity" is generally measured against nonspecific background binding. Typically, an antibody is considered specific when it binds to the target antigen at least 10 times above background binding.

The serum binding single domain antibody contemplated herein can bind to or otherwise associate with serum albumin in such a way that the binding of said serum albumin molecule to FcRn is not (significantly) reduced or inhibited (i.e. compared to the binding of said serum albumin molecule to FcRn when the single domain antibody is not bound thereto). In this aspect of the invention, by "not significantly reduced or inhibited" is meant that the binding affinity for serum albumin to FcRn (as measured using a suitable assay, such as SPR) is not reduced by more than 50%, preferably not reduced by more than 30%, even more preferably not reduced by more than 10%, such as not reduced by more than 5%, or essentially not reduced at all. In this aspect "not significantly reduced or inhibited" may also mean that the half-life of the serum albumin molecule is not significantly reduced (e.g., is not reduced by more than 50%, preferably not reduced by more than 30%, even more preferably not reduced by more than 10%, such as not reduced by more than 5%, or essentially not reduced at all, as measured using a suitable technique known per se). In some embodiments, the single domain antibody are capable of binding to amino acid residues on serum albumin that are not involved in binding of serum albumin to FcRn.

In some embodiments, the single domain antibody described herein binds to serum albumin selected from HSA, cynomolgus monkeys serum albumin and mouse serum albumin. In some embodiments, the binding affinity towards mouse serum albumin is about weaker than that towards human or cynomolgus serum albumin. In some embodiments, the single domain antibody specifically binds to HSA.

In some embodiments, the single domain antibody described herein binds to serum albumin with sufficient binding affinity. The term "affinity" as used herein refers to the strength of non-covalent interaction between an immunoglobulin molecule (i.e. antibody) or fragment thereof and an antigen. Affinity can be expressed numerically using "Kd" values. In general, a lower Kd value corresponds to a stronger binding. Kd may be determined by using any conventional method known in the art, including but are not limited to radioimmunoassays (RIA), enzyme-linked immunosorbent assays (ELISA), surface plasmon resonance (SPR) method, microscale thermophoresis method, HPLC-MS method and flow cytometry (such as FACS) method. In some embodiment, the antibody disclosed here has a $K_d$ value of $\leq 10^{-6}$ M (e.g. $\leq 5\times10^{-7}$ M, $\leq 2\times10^{-7}$ M, $\leq 10^{-7}$ M, $\leq 5\times10^{-8}$ M, $\leq 2\times10^{-8}$ M, $\leq 10^{-8}$ M, $\leq 5\times10^{-9}$ M, $\leq 4\times10^{-9}$M, $\leq 3\times10^{-9}$M, $\leq 2\times10^{-9}$ M, or $\leq 10^{-9}$ M) with the specific antigen.

In certain embodiments, the single domain antibody provided herein are capable of binding to HSA at a Kd value of $\leq 10^{-5}$M to $1\times10^{-12}$M or less, of $10^{-7}$M to $1\times10^{-12}$M or less, or of $10^{-8}$M to $1\times10^{-12}$M or less. In some embodiments, the Kd is no more than $1\times10^{-7}$M (e.g. no more than $5\times10^{-7}$ M, no more than $2\times10^{-7}$ M, no more than $10^{-7}$ M, no more than $5\times10^{-8}$ M, no more than $2\times10^{-8}$ M, no more than $10^{-8}$ M, no more than $5\times10^{-9}$ M, no more than $4\times10^{-9}$M, no more than $3\times10^{-9}$M, no more than $2\times10^{-9}$ M, or no more than $10^{-9}$ M).

In some embodiments, the single domain antibody provided herein is a humanized antibody. The term "humanized" as used herein means that the single domain antibody comprises CDRs derived from a non-human animal, and FR regions derived from human. A humanized antibody polypeptide is desirable in its reduced immunogenicity in human. A humanized antibody polypeptide is chimeric in its variable regions, as non-human CDR sequences are grafted to human or substantially human FR sequences. Humanization of an antibody polypeptide can be essentially performed by substituting the non-human (such as camelid) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Various single domain antibodies that are capable of specifically binding to HSA with a high affinity are known in the art, such as fully human domain antibodies isolated using phage display, VHH antibodies developed form camelidae family, and VNAR antibodies developed from cartilaginous fish, see Zorzi, A et al, Med Chem Commun, 2019, 10, 1068. Exemplary HSA-binding single domain antibodies are disclosed in U.S. Pat. Nos. 8,188,223B2, 9,067,991B2, 9,321,832B2, PCT application WO2008028977A2, WO2008043822A2, WO2020099871A1, G. Winter, et al, Annu. Rev. Immunol., 1994, 12, 433-455., L. J. Holt, et al., Protein Eng., Des. Sel., 2008, 21(5), 283-288, A. Walker, et al., Protein Eng., Des. Sel., 2010, 23(4), 271-278, L. J. Goodall, et al., PLoS One, 2015, 10(9), e0137065, R. L. O'Connor-Semmes, et al., Clin. Pharmacol. Ther., 2014, 96(6), 704-712, C. Read, et al., Basic Clin. Pharmacol. Toxicol., 2019, 1-8, R. Adams, et al., mAbs, 2016, 8(7), 1336-1346, E. Dave, et al., mAbs, 2016, 8(7), 1319-1335, S. Steeland, et al., Drug Discovery Today, 2016, 21(7), 1076-1113, K. Coppieters, et al., Arthritis Rheum., 2006, 54(6), 1856-1866, M. Van Roy, et al., Arthritis Res. Ther., 2015, 17, 135, C. McMahon, et al., Nat. Struct. Mol. Biol., 2018, 25(3), 289-296, M. R. Muller, et al., mAbs, 2012, 4(6), 673-685, all of which are contemplated within the scope of the disclosure and incorporated by reference.

In some embodiments, the single domain antibody comprises a VHH domain. In some embodiments, the VHH domain is humanized.

In some embodiments, the VHH domain comprises a complementarity determining region 1 (CDR1), CDR2 and CDR3, wherein the CDR1 comprises the sequence of SEQ ID NO: 1 (SFGMS) or a variant thereof having up to 3, 2, or 1 amino acid mutation, a CDR2 comprising the sequence of SEQ ID NO: 2 (SISGSGSDTLYADSVKG) or a variant thereof having up to 3, 2, or 1 amino acid mutation, and/or a CDR3 comprising the sequence of SEQ ID NO: 3 (GGSLSR) or a variant thereof having up to 3, 2, or 1 amino acid mutation, wherein the VHH domain retains the binding specificity to serum albumin, optionally to human serum albumin.

In some embodiments, the VHH domain comprises a complementarity determining region 1 (CDR1) comprising the sequence of SEQ ID NO: 1, a CDR2 comprising the sequence of SEQ ID NO: 2, and a CDR3 comprising the sequence of SEQ ID NO: 3.

In some embodiments, the VHH domain comprises a complementarity determining region 1 (CDR1) consisting of the sequence of SEQ ID NO: 1, a CDR2 consisting of the sequence of SEQ ID NO: 2, and a CDR3 consisting of the sequence of SEQ ID NO: 3.

In some embodiments, the VHH domain comprises the sequence of SEQ ID NO: 4, or a variant thereof having at least 70% (e.g. at least 75%, 80%, 85%, 90%, 95%, 99%) identity to SEQ ID NO: 4, wherein the variant retains the binding specificity and/or affinity to serum albumin.

In some embodiments, the variant of SEQ ID NO: 4 has up to 10, 9, 8, 7, 6, 5, 4, 3, 2, or 1 amino acid mutation relative to SEQ ID NO: 4.

In certain embodiments, the serum albumin binding single domain antibody further comprises an N-terminal extension attached to the VHH domain. In certain embodiments, the N-terminal extension comprises amino acid residues of SG, AG, S or A. In certain embodiments, the N-terminal extension comprises a tag, optionally a cleavable tag. Without wishing to be bound by any theory, it is believed that certain N-terminal extension can be useful for expression and post-translational processing.

In certain embodiments, the serum albumin binding single domain antibody does not comprise an N-terminal extension attached to the VHH domain. For example, the VHH domain can be attached to a cleavable tag which, after cleavage, is no longer present in the final product.

In certain embodiments, the serum albumin binding single domain antibody comprises a sequence selected from SEQ ID NO: 4-8.

In some embodiments, the first polypeptide fragment comprising one or more serum albumin binding single domain antibody.

One of ordinary skill in the art will appreciate that various amino acid substitutions, e.g., conservative amino acid substitutions, may be made in the sequence of any of the polypeptide fragment described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

GDF15

The term "GDNF receptor alpha like (GFRAL) receptor" or "GFRAL receptor" or "glial cell line-derived neurotrophic factor receptor alpha like (GFRAL) receptor" refers to a receptor for GDF15 to recognize and bind so as to initiate a signal transduction as described in WO2017/121865, the disclosure of which is incorporated herein to its entirety.

The term "GDNF receptor alpha like (GFRAL) receptor agonist" or "GFRAL receptor agonist" as used herein refers to a molecule which, by itself or by its dimer or multimer, is capable of binding to and activating the GFRAL receptor. A GFRAL receptor agonist may elicit a magnitude of GFRAL receptor response that is similar to or partial of a natural ligand.

A GFRAL receptor agonist can include both a natural ligand of the receptor and an artificially designed or modified molecules that exhibits agonist activity comparable to or no less than 30%, 40% or 50% of that of the natural ligand. In certain embodiments, the GFRAL receptor agonist include, without limitation, GDF15 (including its monomer and dimer), and those disclosed in WO 2017/109706, WO 2013/148117, WO 2014/120619, WO 2012/138919, WO 2013/113008, WO 2015/017710, the disclosure of which are incorporated herein to their entirety.

In certain embodiments, the GFRAL receptor agonist comprises GDF15.

The term "Growth Differentiation Factor 15" or "GDF15" as used herein is intended to broadly encompass the mature domain of the native GDF15 monomer peptide, its homodimer, and all its functional forms such as its functional variants, fragments, fusions, derivatives and mimetics. The full length native GDF15 peptide consists of 308 amino acid residues (NCI Ref. Seq. NP_004855.2), with amino acids 1-29 being a signal peptide, amino acids 30-196 being a pro-domain, and amino acids 197-308 being a mature domain of 112 amino acids. The GDF15 provided in the present disclosure can be the 112 amino acid mature domain of the full length native GDF15 monomer, dimer, or functional variants, fragments, fusions, derivatives or mimetics thereof.

The mature GDF15 peptide contains nine cysteine residues that form four intrachain disulfide bonds and one interchain disulfide bond that gives rise to a covalently linked homodimer. In other words, biologically active GDF15 is a homodimer of the mature peptide covalently linked by one interchain disulfide bond. The term "GDF15" as used herein also includes monomer, multimer, more particularly dimer of the protein.

A functional form of the mature domain of the native GDF15 polypeptide is capable of activating the GFRAL receptor at a level comparable to, or no less than about 20% (or no less than 30%, 40%, 50%, 60%, 70%, 80%, 90%) of, that of the mature domain of the native GDF15 polypeptide. Activation of the GFRAL receptor can lead to biological activities such as, for example, the ability to lower blood glucose, insulin, triglyceride, or cholesterol levels; the ability to reduce body weight; or the ability to improve glucose tolerance, lipid tolerance, or insulin sensitivity; the ability to lower urine glucose and protein excretion. Many functional forms of the mature domain of the native GDF15 polypeptide are known in the art, for example, without limitation, those disclosed in WO 2015/197446, WO2017/121865, WO2017/109706, WO2013/148117, WO2014/120619 (definition to the diseases), WO2012/138919, WO2013/113008, WO2015/017710, disclosure of which are incorporated herein by their entirety.

In certain embodiments, the GDF15 provided herein comprises an amino acid sequence having at least 90% sequence identity to SEQ ID NO: 9 while retaining substantial biological activity of SEQ ID NO: 9.

In certain embodiments, the GDF15 comprises no more than 10, 9, 8, 7, 6, 5, 4, 3, 2 substitutions relative to SEQ ID NO: 9 while retaining substantial biological activity of SEQ ID NO: 9. In certain embodiments, the GDF15 comprises at least 2, 3, 4, 5, 6, 7, 8, 9 or 10 substitutions relative to SEQ ID NO: 9 while retaining substantial biological activity of SEQ ID NO: 9.

In certain embodiments, the GDF15 comprises one or more mutations at a position selected from the group consisting of: A1, R2, N3, H6, P11, H18, T19, V20, R21, A30, M43, A47, R53, A54, M57, H66, R67, L68, A75, A81, P85, M86, Q90, T92, and L105, or any combination thereof. For example, it is believed that substitution at N3 is useful to prevent deamidation and substitution at M57 is useful to reduce oxidation. In certain embodiments, the one or more additional substitutions in GDF15 is at a position of N3 and/or M57. In certain embodiments, the one or more mutations comprise a conservative substitution. As used herein, the numbering of the residues in GDF15 is referred to with reference to the 112 amino acid monomer sequence as set forth in SEQ ID NO: 9, where residue 1 is Alanine (A1) and residue 112 is Isoleucine (I112).

In certain embodiments, the GDF15 comprises a mutation of N3 which is selected from the group consisting of: N3Q, N3S, N3E, N3A, N3T, N3P, N3G, N3V, N3H, N3Y, and deletion of N3. In certain embodiments, the GDF15 comprises a substitution of M57 which is M57A, M57E or M57L. In certain embodiments, the GDF15 comprises a substitution of R2 which is R2S, R2A, or R2E.

In certain embodiments, the one or more mutations in GDF15 are selected from the group consisting of: R2S, R2A, R2E, N3S, N3E, N3A, N3T, N3P, N3G, N3V, N3H, N3Y, N3Q, H6D, P11E, H18E, H18Q, T19S, V20L, R21E, A30E, M43L, M43E, A47E, R53E, A54E, M57A, M57E, M57L, H66E, R67E, L68E, A75E, A81E, P85E, M86F, M86A, M86L, Q90E, T92E, L105E, deletion of N3, deletion of N-terminal 1-3 residues (i.e. A1R2N3), or any combination thereof. More suitable mutations that can be made to GDF15 without significantly reducing its biological activity are described in WO2012138919, WO2013148117, WO2014120619, WO2016018931, WO2017202936, and WO2018215525, disclosure of which is incorporated herein by their entirety.

In certain embodiments, the second polypeptide fragment provided herein comprises GDF15 comprising or consisting of an amino acid sequence selected from the group consisting of SEQ ID NO: 9-12 and 14.

Linker

In certain embodiments, the fusion polypeptide comprises, from N terminus to C terminus, a serum albumin binding single domain antibody operably linked to GDF15, directly or via a linker.

The term "linker" as used herein can be any suitable bifunctional moiety capable of reacting with at least two entities to be linked, thereby bonding the entities to form one molecule or maintaining association of the entities in sufficiently close proximity. The linker can be integrated in the resulting linked molecule or structure, with or without its reacted functional groups. In certain embodiments, the linker separates a first polypeptide fragment from a second polypeptide fragment, without substantial interference to the respective biological activities of either fragment. Suitable linkers can be, for example without limitation, polypeptide linkers and non-peptide linkers, such as bifunctional chemical moieties, or polymers such as PEG.

A direct linkage can be, for example, a covalent bond such as a peptide bond and a linker can be, for example, a polypeptide linker. In certain embodiments, the fusion polypeptide comprises from N terminus to C terminus, a serum albumin binding single domain antibody, a polypeptide linker and the GDF15.

In certain embodiments, the linker comprises a polypeptide linker. The polypeptide linker can be made up of amino acid residues linked together by peptide bonds. The polypeptide linker can further comprise one or more non-natural amino acids.

In certain embodiments, the polypeptide linker comprises at least 1, 4, 5, 10, 12, 20, 24, 30, 40, 50, 60, 70, 80, 90, 100, 110, 120, 130, 140, 150 or 172 amino acid resides, or more. In certain embodiments, the polypeptide linker has a length of from 1 to 200 (1-200), 1-180, 1-170, 1-160, 1-150, 1-140, 1-130, 1-120, 1-110, 1-100, 1-90, 1-80, 1-70, 1-60, 1-50, 1-40, 4-80, 20-80, 30-80, 40-200, 40-180, 40-170, 40-160, 40-150, 40-140, 40-130, 40-120, 40-110, 40-100, 40-90, or 40-80 amino acid residues. Without wishing to be bound by any theory, it is believed that a suitable length of the polypeptide linker can further improve the biological activity or stability or pharmacokinetic parameters of the linked polypeptide molecule.

In certain embodiments, the polypeptide linker has a length of 4, 8, 12, 16, 20, 24, 28, 32, 36, 40, 44, 48, 50, 52, 56, 60, 64, 68, 70, 72, 76 or 80 amino acid residues.

Any suitable polypeptide linkers can be used. For example, the polypeptide linker may comprise or consist of amino acid residues selected from the amino acids glycine (G), glutamine (Q), alanine (A), glutamic acid (E), proline (P), Threonine (T), serine (S), methionine (M), or asparagine (N). In some embodiments, the polypeptide linker can be made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)).

In certain embodiments, the polypeptide linker comprises at least one acidic amino acid residue. Acidic amino acid residue refers to an amino acid residue having an acidic side chain that contains a carboxylic acid group with a pKa between 3.5 and 4.5. Exemplary acidic amino acid residues include, but not limited to, aspartic acid and glutamic acid. In certain embodiments, the at least one acidic amino acid residue comprises aspartic acid or glutamic acid.

In certain embodiments, the polypeptide linker comprises or consists of one or more repeats of a repeating sequence. In certain embodiments, the polypeptide linker comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 repeats of a repeating sequence, or within any numerical range defined by any two numbers listed above.

In certain embodiments, the repeating sequence comprises or consists of no more than 4, 5 or 6 types of amino acid residues selected from the group consisting of: G, Q, A, E, P, T and S. In certain embodiments, the repeating sequence comprises or consists of no more than 4, 5 or 6 types of amino acid residues selected from the group consisting of: G, Q, A, E, P, and S. In certain embodiments, the repeating sequence comprises Q. In certain embodiments, the repeating sequence consists of Q and no more than 3, 4 or 5 types of amino acid residues selected from the group consisting of: G, A, E, P, and S.

In certain embodiments, the repeating sequence consists of G, Q, A, E, and P.

In certain embodiments, the repeating sequence comprises or consists of a sequence selected from the group consisting of: SEQ ID NOs: 15-45 and GS.

In certain embodiments, the polypeptide linker comprises or consists of more than one repeating sequence. For example, the polypeptide linker comprises or consists of 2, 3, or 4 different repeating sequences. In certain embodiments, the polypeptide linker comprises or consists of sequential or tandem repeats of the different repeating sequences.

In certain embodiments, the polypeptide linker comprises or consists of (Repeat1)r(Repeat2)s(Repeat3)x(Repeat4)y, wherein:
Repeat1, Repeat2, Repeat3 and Repeat4 are linked via a peptide bond or via one or more amino acid residues;
Repeat1, Repeat2, Repeat3 and Repeat4 independently, comprise or consist of a sequence selected from the group consisting of: SEQ ID NOs: 15-45 and GS, and
r, s, x and y are independently an integer selected from 0 to 30 (e.g. from 0-29, 0-28, 0-27, 0-26, 0-25, 0-24, 0-23, 0-22, 0-21, 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, or 0-1), provided that r, s, x and y are not 0 at the same time.

In certain embodiments, x and y are 0, r, and s are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 and Repeat2 are a combination selected from the group consisting of:
   (a) Repeat1 comprises or consists of a sequence of SEQ ID NO: 15, Repeat2 comprises or consists of a sequence of SEQ ID NO: 18;
   (b) Repeat1 comprises or consists of a sequence of SEQ ID NO: 17, Repeat2 comprises or consists of a sequence of SEQ ID NO: 18;
   (c) Repeat1 comprises or consists of a sequence of SEQ ID NO: 18, Repeat2 comprises or consists of a sequence of SEQ ID NO: 17;
   (d) Repeat1 comprises or consists of a sequence of SEQ ID NO: 18, Repeat2 comprises or consists of a sequence of SEQ ID NO: 15;
   (e) Repeat1 comprises or consists of a sequence of SEQ ID NO: 19, Repeat2 comprises or consists of a sequence of SEQ ID NO: 18;
   (f) Repeat1 comprises or consists of a sequence of SEQ ID NO: 40, Repeat2 comprises or consists of a sequence of SEQ ID NO: 18;
   (g) Repeat1 comprises or consists of a sequence of SEQ ID NO: 18, Repeat2 comprises or consists of a sequence of SEQ ID NO: 38 and
   (h) Repeat1 comprises or consists of a sequence of SEQ ID NO: 40, Repeat2 comprises or consists of a sequence of SEQ ID NO: 17.

In certain embodiments, r, x and y are 0, s is an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 comprises or consists of a sequence of SEQ ID NO: 7.

In certain embodiments, y is 0, r, s and x are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1, Repeat2 and Repeat3 are a combination selected from the group consisting of:
   (j) Repeat1 comprises or consists of a sequence of SEQ ID NO: 18, Repeat2 comprises or consists of a sequence of SEQ ID NO: 19, and Repeat3 comprises or consists of a sequence of SEQ ID NO: 18;
   (k) Repeat1 comprises or consists of a sequence of SEQ ID NO: 18, Repeat2 comprises or consists of a sequence of SEQ ID NO: 17, and Repeat3 comprises or consists of a sequence of SEQ ID NO: 18;
   (l) Repeat1 comprises or consists of a sequence of SEQ ID NO: 40, Repeat2 comprises or consists of a sequence of SEQ ID NO: 17, and Repeat3 comprises or consists of a sequence of SEQ ID NO: 18;
   (m) Repeat1 comprises or consists of a sequence of SEQ ID NO: 40, Repeat2 comprises or consists of a sequence of SEQ ID NO: 18, and Repeat3 comprises or consists of a sequence of SEQ ID NO: 17;
   (n) Repeat1 comprises or consists of a sequence of SEQ ID NO: 15, Repeat2 comprises or consists of a sequence of SEQ ID NO: 28, and Repeat3 comprises or consists of a sequence of SEQ ID NO: 18;
   (o) Repeat1 comprises or consists of a sequence of SEQ ID NO: 18, Repeat2 comprises or consists of a sequence of SEQ ID NO: 38, and Repeat3 comprises or consists of a sequence of SEQ ID NO: 15;
   (p) Repeat1 comprises or consists of a sequence of SEQ ID NO: 18, Repeat2 comprises or consists of a sequence of SEQ ID NO: 15, and Repeat3 comprises or consists of a sequence of SEQ ID NO: 18;
   (q) Repeat1 comprises or consists of a sequence of SEQ ID NO: 17, Repeat2 comprises or consists of a sequence of SEQ ID NO: 15, and Repeat3 comprises or consists of a sequence of SEQ ID NO: 17; and
   (r) Repeat1 comprises or consists of a sequence of SEQ ID NO: 18, Repeat2 comprises or consists of a sequence of SEQ ID NO: 15, and Repeat3 comprises or consists of a sequence of SEQ ID NO: 38.

In certain embodiments, r, s, x and y are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1, Repeat2, Repeat 3 and Repeat 4 are a combination selected from the group consisting of:

(a) Repeat1 comprises or consists of a sequence of SEQ ID NO: 18, Repeat2 comprises or consists of a sequence of SEQ ID NO: 20, Repeat3 comprises or consists of a sequence of SEQ ID NO: 17, and Repeat4 comprises or consists of a sequence of SEQ ID NO: 18;

(b) Repeat1 comprises or consists of a sequence of SEQ ID NO: 15, Repeat2 comprises or consists of a sequence of SEQ ID NO: 38, Repeat3 comprises or consists of a sequence of SEQ ID NO: 15, and Repeat4 comprises or consists of a sequence of SEQ ID NO: 18;

(c) Repeat1 comprises or consists of a sequence of SEQ ID NO: 18, Repeat2 comprises or consists of a sequence of SEQ ID NO: 38, Repeat3 comprises or consists of a sequence of SEQ ID NO: 15, and Repeat4 comprises or consists of a sequence of SEQ ID NO: 18;

(d) Repeat1 comprises or consists of a sequence of SEQ ID NO: 18, Repeat2 comprises or consists of a sequence of SEQ ID NO: 28, Repeat3 comprises or consists of a sequence of SEQ ID NO: 18, and Repeat4 comprises or consists of a sequence of SEQ ID NO: 15; and (e) Repeat1 comprises or consists of a sequence of SEQ ID NO: 18, Repeat2 comprises or consists of a sequence of SEQ ID NO: 15, Repeat3 comprises or consists of a sequence of SEQ ID NO: 39, and Repeat4 comprises or consists of a sequence of SEQ ID NO: 38.

In certain embodiments, the polypeptide linker comprises an amino acid sequence selected from the group consisting of SEQ ID NOs: 17 and 46-49. In certain embodiments, the polypeptide linker comprises an amino acid sequence selected from the group consisting of SEQ ID NOs: 48-49.

In certain embodiments, the fusion polypeptide provided herein comprise an amino acid sequence selected from the group consisting of: SEQ ID NOs: 50-59 and 13.

Table 1 below shows the SEQ ID NOs of the exemplary fusion polypeptide sequences, and the SEQ ID NOs for the serum albumin binding single domain antibody, linker and GDF15 sequences contained in the fusion polypeptides provided herein. Table 1 below also shows the mutations in the serum albumin binding single domain antibody, and in the GDF15, as well as the repeating sequences and number of repeats in the linker sequences.

TABLE 1

Exemplary fusion polypeptide sequences

| Molecule | SEQ ID NO | Mutations in single domain antibody** | Linker | Mutations in GDF15# |
|---|---|---|---|---|
| Fusion Protein 1 | 50 | −1A (SEQ ID NO: 5) | (GAQP)3(GQEP)7 (SEQ ID NO: 49) | N3Q, M57L (SEQ ID NO: 10) |
| Fusion Protein 2 | 51 | −1A (SEQ ID NO: 5) | (GAQP)8(GQEPGAQP)6 (SEQ ID NO: 48) | N3Q, M57L (SEQ ID NO: 10) |
| Fusion Protein 3 | 52 | −1S (SEQ ID NO: 6) | (GAQP)3(GQEP)7 (SEQ ID NO: 49) | N3Q, M57L (SEQ ID NO: 10) |
| Fusion Protein 4 | 53 | −2A, −1G (SEQ ID NO: 7) | (GAQP)3(GQEP)7 (SEQ ID NO: 49) | N3Q, M57L (SEQ ID NO: 10) |
| Fusion Protein 5 | 54 | −2S, −1G (SEQ ID NO: 8) | (GAQP)3(GQEP)7 (SEQ ID NO: 49) | N3Q, M57L (SEQ ID NO: 10) |
| Fusion Protein 6 | 55 | −2S, −1G (SEQ ID NO: 8) | (GAQP)8(GQEPGAQP)6 (SEQ ID NO: 48) | N3Q, M57L (SEQ ID NO: 10) |
| Fusion Protein 7 | 56 | −2S, −1G (SEQ ID NO: 8) | (GQEP)5 (SEQ ID NO: 47) | N3Q, M57L (SEQ ID NO: 10) |
| Fusion Protein 8 | 57 | −2S, −1G (SEQ ID NO: 8) | (GQEP)2 (SEQ ID NO: 46) | N3Q, M57L (SEQ ID NO: 10) |
| Fusion Protein 9 | 58 | −2S, −1G (SEQ ID NO: 8) | (GQEP) (SEQ ID NO: 17) | N3Q, M57L (SEQ ID NO: 10) |
| Fusion Protein 10 | 59 | Native (SEQ ID NO: 4) | (GAQP)3(GQEP)7 (SEQ ID NO: 49) | N3Q, M57L (SEQ ID NO: 10) |
| Fusion Protein 11 | 13 | Native (SEQ ID NO: 4) | (GAQP)8(GQEPGAQP)6 (SEQ ID NO: 48) | N3Q, M57L (SEQ ID NO: 10) |
| Fusion Protein 12 | 60 | −2S, −1G (SEQ ID NO: 8) | (GAQP)2(GQEP)7(GAQP) (SEQ ID NO: 61) | N3Q, M57L (SEQ ID NO: 10) |

**Mutations in single domain antibody means mutations relative to SEQ ID NO: 4, wherein the first residue is E1, and the last residue is S116; −1 position refers to the first residue extended from the N-terminus of SEQ ID NO: 4, and −n position refers to the $n^{th}$ residue extended from the N-terminus of SEQ ID NO: 4.
Mutations in GDF15 means mutations relative to SEQ ID NO: 9, wherein the first residue is A1, and the last residue is I112;

Polypeptide Complex

In another aspect, the present disclosure provides a polypeptide complex comprising a dimer of the fusion polypeptide provided herein.

The term "polypeptide complex(es)" as used herein, means a complex comprises two or more fusion polypeptides, polypeptides or polypeptide fragments held together by covalent interactions (e.g. disulfide bond between cysteines) or non-covalent interactions. A polypeptide complex can be generated naturally or synthetically. The two or more fusion polypeptides, polypeptides or polypeptide fragments in the polypeptide complex may be the same or different. In certain embodiments, the polypeptide complex is a homodimer.

In certain embodiments, the dimer is associated with a disulfide bond. In certain embodiments, the disulfide bond is formed between the second polypeptide fragments comprising the GDF15.

Method of Preparation

The present disclosure provides isolated nucleic acids or polynucleotides that encode the fusion polypeptide provided herein or the polypeptide complex provided herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the fusion polypeptide provided herein or the polypeptide complex provided herein can be constructed using recombinant techniques. To this end, DNA encoding the serum albumin binding single domain antibody (such as VHH domain specific for HSA) and DNA encoding the GFARL agonist (such as GFD 15) fusion polypeptide or the polypeptide complex can be obtained and operably linked to allow transcription and expression in a host cell to produce the fusion polypeptide. If needed, polynucleotide sequences encoding for one or more linkers are also operably linked to allow expression of the desired product.

The encoding polynucleotide sequences can be further operably linked to one or more regulatory sequences, optionally in an expression vector, such that the expression or production of the fusion polypeptides or polypeptide complexes is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, lpp, npr, pac, syn, trc and T3, or eukaryotic promoters such as SV40, CMV, and EF-1α), and a transcription termination sequence.

Vectors and Host Cells

In another aspect, the present disclosure provides a vector comprising the polynucleotide of provided herein.

Vectors comprising the polynucleotide sequence(s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell or eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis, Pseudomonas such as P. aeruginosa, and Streptomyces. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the serum albumin binding single domain antibody/GDF15 fusion polypeptide can be subcloned into an expression vector, which is expressed as inclusion bodies in the host cells. The vector can be a viral vector, and any suitable viral vector can be used in this capacity.

In another aspect, the present disclosure provides a host cell comprising the vector provided herein. The host cell is prokaryotic cell or a eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the polypeptide complex provided herein, comprising culturing the host cell provided herein under a condition that allows expression of the polynucleotide provided herein.

For production of the fusion polypeptide or polypeptide complex provided herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the fusion polypeptide and/or polypeptide complex provided herein, comprising culturing the host cell provided herein under the condition at which the fusion polypeptide and/or the polypeptide complex is expressed.

In certain embodiments, the polypeptide complex is expressed as inclusion bodies. In certain embodiments, the method further comprises renaturing the polypeptide complex from the inclusion bodies.

When using recombinant techniques, the fusion polypeptide and the polypeptide complex provided herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the fusion polypeptide and/or polypeptide complex.

The fusion polypeptide and the polypeptide complex provided herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

Pharmaceutical Composition

In another aspect, the present disclosure also provides a pharmaceutical composition comprising the fusion polypeptide, or polypeptide complex provided herein and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the fusion polypeptide, the polypeptide complex or the conjugate disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the fusion polypeptide, the polypeptide complex or the conjugate as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the fusion polypeptide, the polypeptide complex, or the conjugate provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Administration of the pharmaceutical composition as described herein may be via any route known to be effective by the physician of ordinary skill. One example is peripheral parenteral administration by a sterile syringe or some other mechanical device such as an infusion pump. In certain embodiments, peripheral parenteral route is intravenous, intramuscular, subcutaneous, or intraperitoneal routes of administration.

In certain embodiments, the fusion polypeptide, the polypeptide complex, or the conjugate described herein is formulated in a form suitable for non-parenteral routes administration, such as oral, rectal, nasal, or lower respiratory routes administration.

In certain embodiments, the fusion polypeptide or the polypeptide complex described herein is formulated in a solid formulation such as lyophilization or spray drying, which is then reconstituted in a suitable diluent solution prior to administration. Standard pharmaceutical formulation techniques, such as those described in Remington: The Science and Practice of Pharmacy (D. B. Troy, Editor, 21st Edition, Lippincott, Williams & Wilkins, 2006), may be employed. Alternatively, the fusion polypeptide, the polypeptide complex, or the conjugate described herein can be formulated for administration through the lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, transdermal, or pulmonary route. As a still further option, the fusion polypeptide, the polypeptide complex, or the conjugate described herein can be formulated for administration through transdermal administration, for example, by needle-free injection or from a patch, optionally an iontophoretic patch, or transmucosal, for example, buccal, administration.

Method of Treatment

In another aspect, the present disclosure provides a method of preventing or treating a metabolic disorder in a subject in need thereof, comprising administering a therapeutically effective amount of the fusion polypeptide provided herein, or the polypeptide complex provided herein.

Therapeutic methods are also provided, comprising: administering a therapeutically effective amount of the fusion polypeptide, or the polypeptide complex provided herein to a subject in need thereof, thereby treating or preventing a condition or a disorder. In certain embodiments, the subject has been identified as having a disorder or condition likely to respond to the fusion polypeptide, or the polypeptide complex provided herein.

In certain embodiments, the metabolic disorder is diabetes, obesity, non-alcoholic steatohepatitis (NASH), cardiovascular like dyslipidemia, artherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

For example, a metabolic condition or disorder that can be treated or ameliorated using the fusion polypeptide, or the polypeptide complex provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 mutant polypeptide can also be found in the American Diabetes Association Standards of Medical Care in Diabetes Care-2011, American Diabetes Association, Diabetes Care Vol. 34, No. Supplement 1, SI 1-S61, 2010, incorporated herein by reference.

The therapeutically effective amount of the fusion polypeptide and the polypeptide complex provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the fusion polypeptide, the polypeptide complex and the conjugate provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the fusion polypeptide, or the polypeptide complex o provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the fusion polypeptide, or the polypeptide complex provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The fusion polypeptide, or the polypeptide complex provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

The fusion polypeptide, or the polypeptide complex may be administered alone or in combination with one or more additional therapeutic means or agents.

In certain embodiments, when used for treating a metabolic disease, the fusion polypeptide, or the polypeptide complex provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art. A non-limiting list of examples of compounds that can be administered in combination with a pharmaceutical composition includes rosiglitizone, pioglitizone, repaglinide, nateglitinide, metformin, exenatide, stiagliptin, pramlintide, glipizide, glimepriride acarbose, and miglitol.

Kit

Also provided are kits for practicing the disclosed methods. Such kits can comprise a pharmaceutical composition such as those described herein, including nucleic acids encoding the fusion polypeptides, or the polypeptide complex provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a fusion polypeptide, or a polypeptide complex; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular like dyslipidemia, artherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Example 1: Recombinant Expression of Fusion Proteins

The GDF15 fusion polypeptides listed in Table 1 were produced from bacterial *E. coli* expression system as homodimers, using BL21(DE3) derivative strain. The DNA coding for the GDF15 fusion precursors was codon optimized for *E. coli* expression, de novo synthesized and subcloned into PET derivative expression vectors (Novagen). Amino acid substitutions were accomplished by modification of the corresponding genetic codes. Overexpression of GDF15 fusion protein complexes as inclusion bodies was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours. The quality of inclusion bodies was analyzed with microscopic imaging.

Example 2: Refolding and Purification

Cells were harvested as described in Example 1 and lysed in 20 mM Tris pH8.0, 0.15M NaCl buffer by cell disruptor (900 bar, for twice). The insoluble fractions, containing the fusion proteins (i.e. homodimers), were collected and washed in the same buffer twice by centrifugation (8,000×g, for 30 min). The 8M urea with 10 mM DTT buffer was then used to solubilize the inclusion bodies. After 1 hours, the solutions were diluted 20-fold with refolding buffer. The refolding samples were stirred at the room temperature for 12 hours. After removing tag by protease, the proteins were loaded on to anion exchange chromatography using Source 30Q resin (GE healthcare) running with gradient elution with 20 mM Tris 9.0 and 0.5 M NaCl. In some instances, further polishing was performed by hydrophobic interaction chromatography. The samples in each step were characterized by LC/MS to confirm the correct molecular weight.

Example 3: In Vitro Activities of the Fusion Proteins

Method:

The in vitro GDF15 activities of the fusion proteins (i.e. homodimers) were assessed using a cell line overexpressing both human GFRAL, c-Ret receptor and SRE luciferase reporter. The fusion proteins were tested with 3-fold serial dilutions with 5 nM as top concentration. To assess the impact of albumin binding, the fusion proteins were also tested in the presence of 1% HSA. After 3-5 hours treatment, luciferase activities were measured by Steadylite plus kit (Perkin Elmer, 6066751).

The activity of each protein was represented by $EC_{50}$, derived from non-linear regression analysis. Data for a few exemplary protein conjugates were summarized in below Table 2, with native GDF15 as reference.

TABLE 2

In vitro activities of the fusion proteins.

| Molecule | Linker length (aa) | HSA free GDF15 activity (EC50, pM) | 1% HSA GDF15 activity (EC50, pM) |
|---|---|---|---|
| Native GDF15 (SEQ ID NO: 9) | No linker | 10.3 | 8.2 |
| Fusion protein 1 (SEQ ID NO: 50) | 40 | 24.3 | 42.4 |
| Fusion protein 2 (SEQ ID NO: 51) | 80 | 31.2 | 64.9 |
| Fusion protein 5 (SEQ ID NO: 54) | 40 | 34.7 | 67.6 |
| Fusion protein 12 (SEQ ID NO: 59) | 40 | 56.5 | 78.1 |
| Fusion protein 7 (SEQ ID NO: 56) | 20 | 45.9 | 130.0 |
| Fusion protein 8 (SEQ ID NO: 57) | 8 | 43.3 | 151.2 |
| Fusion protein 9 (SEQ ID NO: 58) | 4 | 41.3 | 269.8 |

Conclusion

The Fusion proteins 1, 2, 5, 7, 8, 9 and 12 respectively having the amino acid sequence of SEQ ID NO: 50, 51, 54, 56, 57, 58 and 59, showed comparable in vitro potency with native GDF15 in the cell based assay under HSA free conditions. However, Fusion proteins 7, 8 and 9 showed much lower potency in the assay with the supplement of 1% HSA, implying that albumin binding has significant effect on in vitro potency of Fusion proteins 7, 8 and 9. Albumin binding only have minor effect on in vitro potency of fusion proteins 1, 2, 5 and 12. Therefore, it was unexpectedly found that the linker length determines GDF15 activities in the presence of albumin.

Example 4: In Vivo Activities of the Fusion Protein

Method:

10 week old male C57BL/6 mice were injected everyday subcutaneously with 30 nmol/kg of the fusion proteins for 10 days (n=5/group), semaglutide was studied in parallel as a control. Body weight (BW) was measured daily for each individual animal and food intake was measured daily for each entire treatment group. Day 1 and Day 10 are the first day and the last day of treatment. % BW loss=100*(BW on Day n−BW on Day 1)/(BW on Day 1). Cumulative food intake on Day n represents sum of food intake from Day 1 to Day n. Data are indicated as mean values and standard error (SEM) or pooled values. Body weight reduction on Day 11 is calculated by −1*(% BW loss of treatment group−% BW loss of vehicle group); Cumulative food intake reduction on Day 11 is calculated by −100*(cumulative food intake of treatment group−cumulative food intake of vehicle group)/cumulative food intake of vehicle group.

TABLE 3a

Food intake and body weight reduction in C57 mice at Day 11

| Molecule | Cumulative food intake reduction at 30 nmol/kg (% reduction compared to vehicle) (Day 11) | Body weight reduction at 30 nmol/kg (% reduction compared to vehicle) (Day 11) |
|---|---|---|
| Semaglutide | 11.8 | 7.27 |
| Fusion protein 1 (SEQ ID NO: 50) | 15.9 | 17.77 |
| Fusion protein 2 (SEQ ID NO: 51) | 18.3 | 17.28 |

TABLE 3b

Food intake and body weight reduction in C57 mice at Day 11

| Molecule | Cumulative food intake reduction at 30 nmol/kg (% reduction compared to vehicle) (Day 11) | Body weight reduction at 30 nmol/kg (% reduction compared to vehicle) (Day 11) |
|---|---|---|
| Fusion protein 5 (SEQ ID NO: 51) | 7.3 | 14.05 |
| Fusion protein 12 (SEQ ID NO: 60) | 14.5 | 15.74 |

Conclusion

Figure 1B:
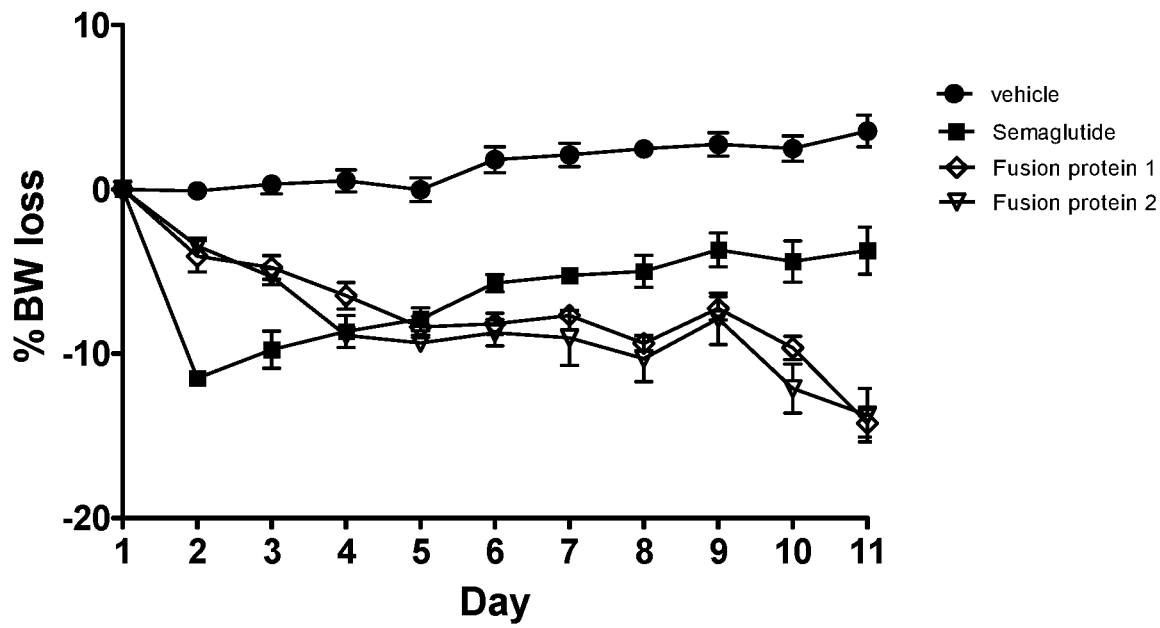
Figure 1C:
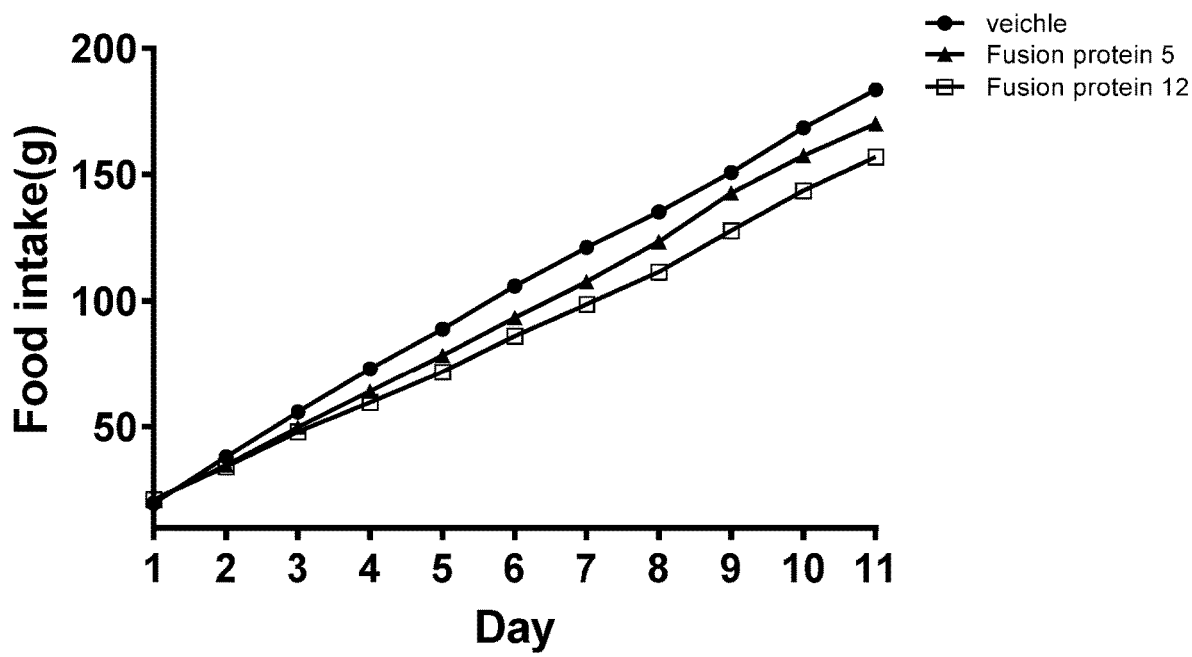
Figure 1D:
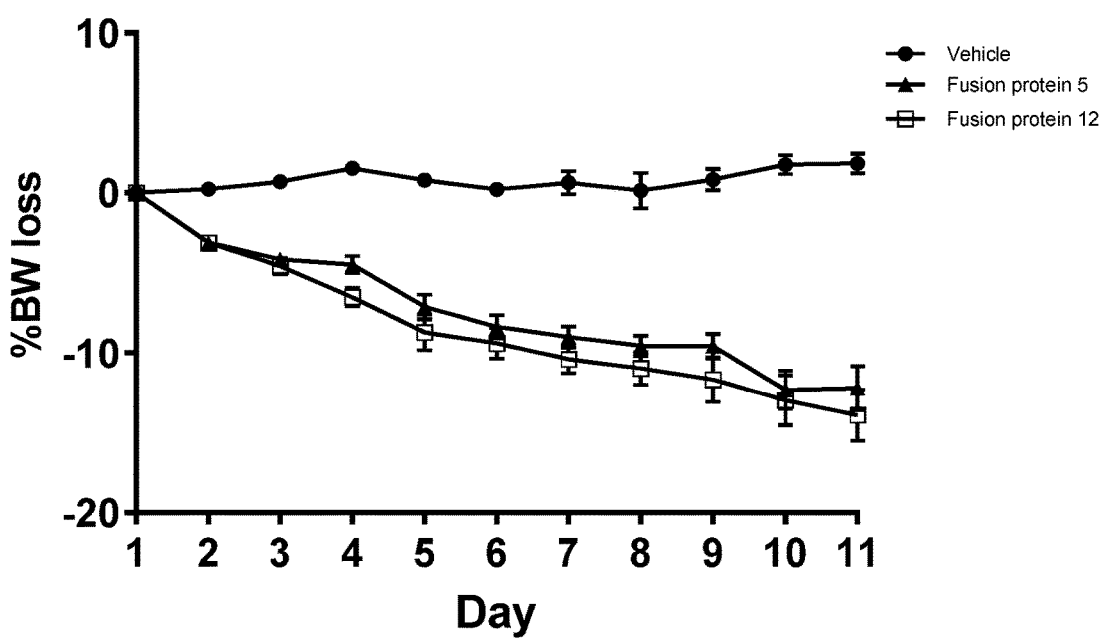

The fusion protein demonstrated better BW reduction efficacy than Semaglutide (FIGS. 1a and 1b and Tables 3a and 3b) at the end of the treatment period.

Example 5: Pharmacokinetic Measurement of the Fusion Protein

Method:

6-8 week old male C57BL/6 mice were administrated in a single subcutaneous dose of 30 nmol/kg of the fusion protein (n=2/group). Plasma samples were collected pre-dose (−5 min), 0.5 hr, 1 hr, 2 hr, 4 hr, 6 hr, 8 hr, 12 hr, 24 hr, 48 hr and 72 hr after the injection. The concentrations of the fusion protein in the plasma were measured with a GDF15 ELISA assay (R&D Systems, DY957).

Conclusion

Figure 2:
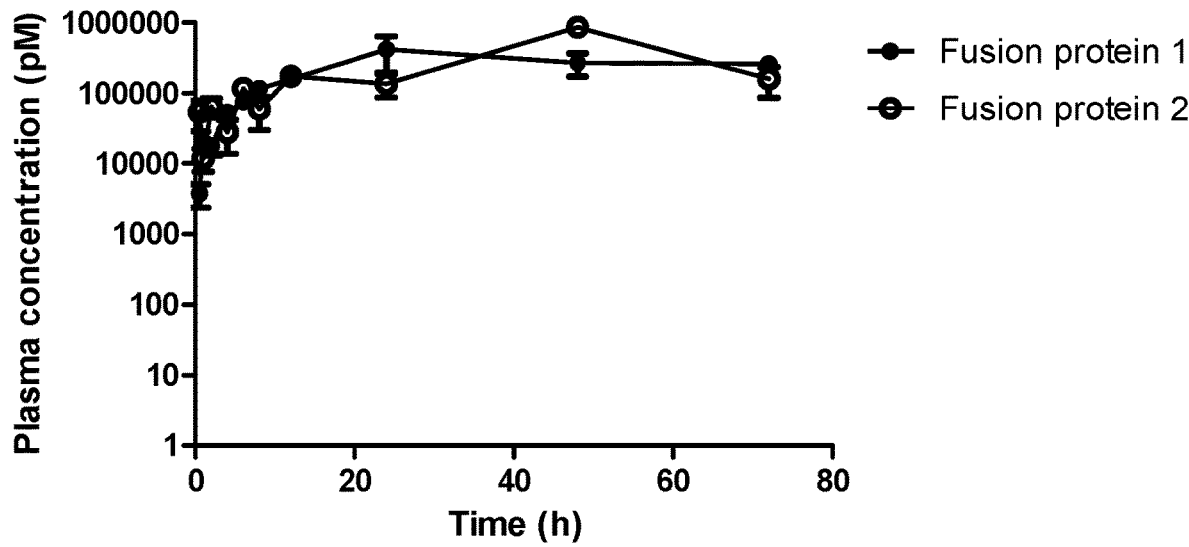
FIG. 2 shows pharmacokinetic measurement of the tested fusion proteins in C57BL/6 mice.

As shown in FIG. 2, both fusion proteins demonstrated high Cmax and long half-life in mice. Due to the short sample collection period, it is difficult to accurately calculate the T½ for each compound, which will be greater than 50 hours.

Example 6: Efficacy Study in Disease Models

Selected molecules are assessed in disease animal models (such DIO mice) to determine body weight, food intake, glucose efficacy with dose responses in chronic studies. Some biomarkers are also measured, including fasting insulin, plasma triglyceride, cholesterol, liver triglyceride, and inflammatory biomarkers (ALT, AST and CRP).

Method:

22 week old DIO male C57BL/6 mice (~40 g) were injected once every day (QD) subcutaneously with fusion proteins (fusion proteins 5 and 12) for 12 days. Food intake and body weight were measured daily. Five animals were used for each treatment group. Body weight was monitored for each individual animal, but food intake for each group animals was measured together and was divided by animal numbers. Day 1 and Day 12 are first day and last day of molecule dosage. Data are indicated as mean values and standard error (SEM) or pooled values. Statistical analysis was performed by One-way ANOVA. Body weight reduction on Day 12 is calculated by −1*(% BW loss−% BW loss of vehicle group); Cumulative food intake reduction is calculated by −100*(cumulative food intake-cumulative food intake of vehicle)/cumulative food intake of vehicle.

Figure 3A:
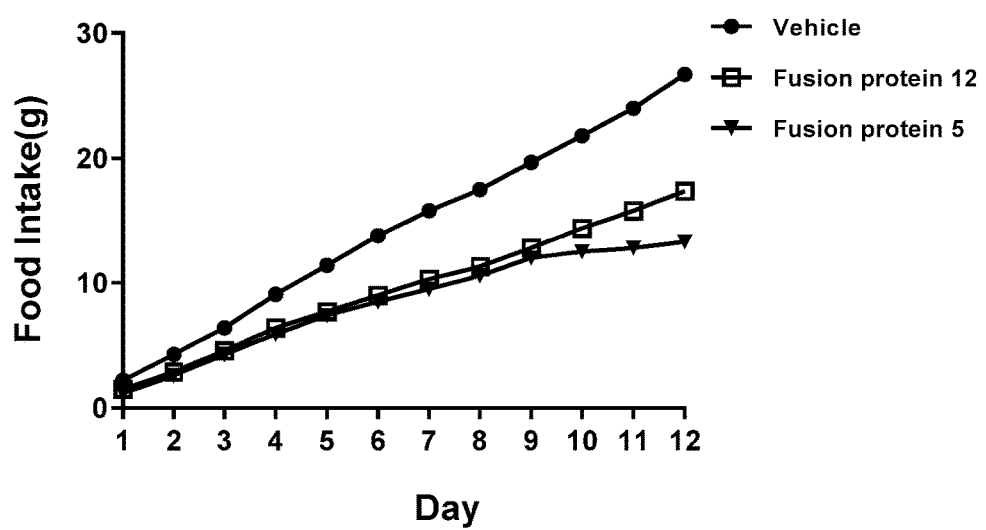
FIGS. 3a and 3b show in vivo efficacy of the tested fusion proteins in DIO mice.
Figure 3B:
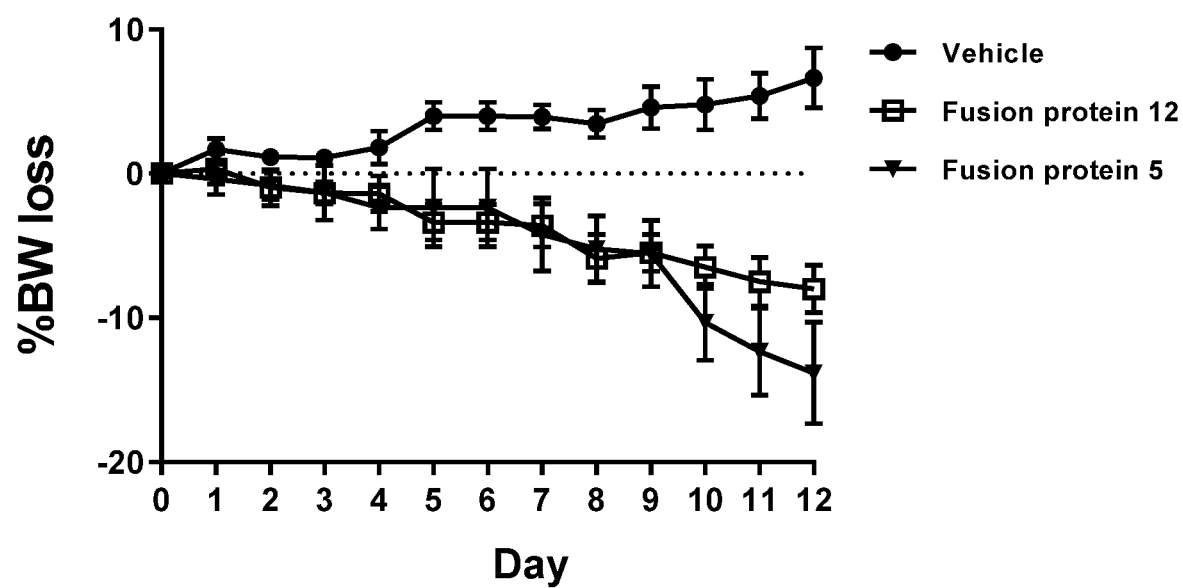

Conclusion: in DIO study, as shown in FIGS. 3a and 3b, Fusion proteins 5 and 12 have significant effect on body weight reduction and food intake suppression.

Example 7: PK Study in Non-Human Primates

Pharmacokinetics of selected molecules are assessed in monkeys. Both subcutaneous and intravenous injections are performed.

Example 8: Immunogenicity Assessment

Selected fusion protein conjugates are also assessed for immunogenicity by in silico (iTope and TCED methods) and ex vivo (EpiScreen) methods.

Example 9: Stability Assessment

To test the stability, the different conjugated fusion proteins are formulated in buffers with different compositions (pH6, 7, 7.4 and 8.0) and stored at different temperatures (such as 25° C. and 37° C.) for 2-4 weeks. The % HMWP and % LMW are analyzed by size exclusion chromatography (SEC)-HPLC. The concentration and modifications were analyzed by reverse phase (RP)-UPLC and LC/MS.

---

The invention claimed is:

1. A fusion polypeptide comprising, from N terminus to C terminus, a serum albumin binding single domain antibody, a polypeptide linker and a GDF15:
wherein the single domain antibody comprises a VHH domain, wherein the VHH domain comprises a complementarity determining region 1 (CDR1) comprising the sequence of SEQ ID NO: 1, a CDR2 comprising the sequence of SEQ ID NO: 2, and a CDR3 comprising the sequence of SEQ ID NO: 3; and wherein the polypeptide linker has a length of 40-80 amino acid residues, wherein the polypeptide linker comprises an amino acid sequence selected from the group consisting of SEQ ID NOs: 48-49 and 61.

2. The fusion polypeptide of claim 1, wherein the VHH domain comprises the sequence of SEQ ID NO: 4, or a variant thereof having 70%-99% identity to SEQ ID NO: 4, wherein the variant retains the binding specificity and/or affinity to serum albumin.

3. The fusion polypeptide of claim 2, wherein the serum albumin binding single domain antibody further comprises an N-terminal extension attached to the VHH domain.

4. The fusion polypeptide of claim 3, wherein the N-terminal extension comprises amino acid residues of SG, AG, S or A.

5. The fusion polypeptide of claim 2, wherein the serum albumin binding single domain antibody comprises an amino acid sequence selected from SEQ ID NOs: 4-8.

6. The fusion polypeptide of claim 1, wherein the GDF15 comprises one or more mutations at a position selected from the group consisting of: A1, R2, N3, H6, P11, H18, T19, V20, R21, A30, M43, A47, R53, A54, M57, H66, R67, L68, A75, A81, P85, M86, Q90, T92, and L105, or any combination thereof, relative to SEQ ID NO: 9, while retaining substantial biological activity of SEQ ID NO: 9.

7. The fusion polypeptide of claim 6, wherein the one or more mutations in GDF15 comprises:
  1) mutation of N3 selected from the group consisting of: N3Q, N3S, N3E, N3A, N3T, N3P, N3G, N3V, N3H, N3Y and deletion of N3; and/or
  2) substitution of M57 selected from the group consisting of: M57A, M57E and M57L; and/or
  3) substitution of M86L or M86A.

8. The fusion polypeptide of claim 6, wherein the one or more mutations in GDF15 are selected from the group consisting of: R2S, R2A, R2E, N3S, N3E, N3A, N3T, N3P, N3G, N3V, N3H, N3Y, N3Q, H6D, P11E, H18E, H18Q, T19S, V20L, R21E, A30E, M43L, M43E, A47E, R53E, A54E, M57A, M57E, M57L, H66E, R67E, L68E, A75E, A81E, P85E, M86F, M86A, M86L, Q90E, T92E, L105E, deletion of N3, and deletion of N-terminal 1-3 residues, or any combination thereof, relative to SEQ ID NO: 9.

9. The fusion polypeptide of claim 6, wherein the GDF15 comprises or consists of an amino acid sequence selected from the group consisting of SEQ ID NOs: 9-12 and 14.

10. The fusion polypeptide of claim 1, comprising an amino acid sequence selected from the group consisting of: SEQ ID NOs: 50-55, 59-60 and 13.

11. A polypeptide complex comprising a dimer of the fusion polypeptide of claim 1.

12. The polypeptide complex of claim 11, which is a homo-dimer associated with a disulfide bond.

13. The polypeptide complex of claim 12, wherein the disulfide bond is formed between the second polypeptide fragments comprising the GDF15.

14. A polynucleotide encoding the fusion polypeptide of claim 1.

15. A vector comprising the polynucleotide of claim 14.

16. A host cell comprising the vector of claim 15.

17. The host cell of claim 16, wherein the host cell is a prokaryotic cell or eukaryotic cell.

18. A method of producing a polypeptide complex comprising a dimer of the fusion polypeptide of claim 1, comprising culturing the host cell comprising the vector comprising the polynucleotide encoding the fusion polypeptide of claim 1.

19. The method of claim 18, wherein the host cell is prokaryotic cell or a eukaryotic cell.

20. The method of claim 19, wherein the polypeptide complex is expressed as inclusion bodies.

21. The method of claim 20, wherein the method further comprises renaturing the polypeptide complex from the inclusion bodies.

22. A pharmaceutical composition comprising the polypeptide complex of claim 11 and a pharmaceutically acceptable carrier.

23. A method of treating a metabolic disorder in a subject in need thereof, comprising administering a therapeutically effective amount of the polypeptide complex of claim 11; wherein the metabolic disorder is diabetes, obesity, nonalcoholic steatohepatitis (NASH), cardiovascular like dyslipidemia, artherosclerosis, alcoholic steatohepatitis (ASH), diabetic nephropathy, gestational diabetes, metabolic syndrome, nonalcoholic fatty liver disease (NAFLD), end-stage liver disease, hepatic steatosis (fatty liver), liver cirrhosis, or primary biliary cirrhosis (PBC).

* * * * *